(12) United States Patent
Schiffer et al.

(10) Patent No.: US 6,664,055 B2
(45) Date of Patent: Dec. 16, 2003

(54) KAINATE RECEPTOR SUBUNIT GLUR7 POLYMORPHISMS FOR DETERMINING PREDISPOSITIONS TO RECURRENT UNIPOLAR AND BIPOLAR II DEPRESSIVE DISORDERS

(75) Inventors: Hans H. Schiffer, San Diego, CA (US); Stephen F. Heinemann, La Jolla, CA (US)

(73) Assignee: The Salk Institute, La Jolla, CA (US)

( * ) Notice: Subject to any disclaimer, the term of this patent is extended or adjusted under 35 U.S.C. 154(b) by 0 days.

(21) Appl. No.: 09/854,140

(22) Filed: May 11, 2001

(65) Prior Publication Data

US 2003/0033619 A1 Feb. 13, 2003

(51) Int. Cl.[7] .......................... C12Q 1/68; C12P 19/34; C07H 21/02; C07H 21/04
(52) U.S. Cl. ........................ 435/6; 435/91.2; 536/23.5; 536/24.31; 536/24.33
(58) Field of Search ................ 435/91.1, 91.2, 435/6; 536/23.1, 24.1; 800/21

(56) References Cited

U.S. PATENT DOCUMENTS

| | | |
|---|---|---|
| 5,863,734 A | 1/1999 | Karayiorgou et al. |
| 5,998,133 A | 12/1999 | Blumenfeld et al. |
| 6,080,549 A | 6/2000 | Deth |

OTHER PUBLICATIONS

Schiffer et al. "Unequal Expression of Allelic Kainate . . . " Journal of Neuroscience 2000, 20(24):9025–9033.*
Seta et al. "Expression of p53 and p21 WAF1/CIP1 . . ." Digestive Diseases and Sciences, 1998 43 (2) 279–289.*
Chittajallu et al., "Kainate receptors: subunits, synaptic localization and function," *TIPS* 20:26–35 (1999).

Frerking et al., "Synaptic kainate receptors," *Curr. Opin. Neurobiol.* 10:342–351 (2000).

Nakanishi et al., "Glutamate receptors: brain function and signal transduction," *Brain Res. Rev.* 26:230–235 (1998).

Schiffer, Hans H. et al., "Unequal Expression of Allelic Kainate Receptor GluR7 mRNAs in Human Brains," *J. Neurosci.* 20(24):9025–9033 (2000).

Schiffer et al. The Journal of Neuroscience, Dec. 15, 2000, 20(24):9025–9033.*

* cited by examiner

Primary Examiner—Carla J. Myers
Assistant Examiner—Sally Sakelaris
(74) *Attorney, Agent, or Firm*—Foley & Lardner

(57) ABSTRACT

Provided are methods for determining the predisposition of a subject to a mood disorder by determining in a biological sample of a subject, the presence of a kainate receptor subunit GluR7 allelic genotype or allelic phenotype associated with predisposition to a mood disorder. The allelic genotype is homozygosity for a thymine containing nucleotide at position 928 (928T/T) or homozygosity for a guanine containing nucleotide position 928 (928G/G). In addition, a predominant expression of one GluR7 allele over the other allele in a heterozygous individuals also predicts predisposition to a mood disorder. The present invention also includes a method of treating or preventing a mood disorder and methods for identifying a compound useful for treatment. Transgenic non-human animals that express only a particular human GluR7 allele at nucleotide position 928 also are provided as a model of a human mood disorder.

10 Claims, No Drawings

SEQUENCE LISTING

<160> NUMBER OF SEQ ID NOS: 14

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 1
ctggcctgag agcctgctgg cttc                                          24

<210> SEQ ID NO 2
<211> LENGTH: 24

```
<212> TYPE: DNA
<213> ORGANISM: Artificial Sequence
<220> FEATURE:
<223> OTHER INFORMATION: Description of Artificial Sequence: Primer

<400> SEQUENCE: 2
cgggggagcc tgagaggcat gtgc                                               24

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 3
cctaccgcta ctcaggcgtg aacc                                               24

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 4
ttcttctttc tgccttctcg gcctt                                              25

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 5
tccttcctca atcccctgtc tccg                                               24

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 6
acacagctga cacccaggta ggca                                               24

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 7
ttcccattga gcctccttga tgaag                                              25

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 8
```

-continued

```
atgaagcggc cgccaaagcg c                                              21

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 9
tcaggcgtga acctgacagg attc                                           24

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 10
gaccatcacc catgtccgag agaa                                           24

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 11
ggagcccatt ccmaccagaa gct                                            23

<210> SEQ ID NO 12
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 12
ggctgcaggc agctccc                                                   17

<210> SEQ ID NO 13
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 13
cgtacatcca gatgtcc                                                   17

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 14
tcacccagcc gccttaccat catc                                           24
```

KAINATE RECEPTOR SUBUNIT GLUR7 POLYMORPHISMS FOR DETERMINING PREDISPOSITIONS TO RECURRENT UNIPOLAR AND BIPOLAR II DEPRESSIVE DISORDERS

STATEMENT AS TO FEDERALLY SPONSORED RESEARCH

This invention was made with Government support under the National Institutes of Health. The government may have certain rights in the invention.

FIELD OF INVENTION

The present invention relates generally to the identification of cell receptors and encoding genes that are involved in neurological disease and the identification of receptors and encoding genes involved in mono and bipolar mood disorders.

BACKGROUND OF THE INVENTION

Mood disorders rank among the top ten causes of disability worldwide. Unipolar depressive disorder and bipolar disorder are mood disorders with high prevalence in the population and an enormous impact on the life of affected individuals and society (Oruc et al., (1998a) Med. Arch., 52:107–112; Craddock and Jones, (1999) Am. J. Psychiatry, 149443–454; Oruc et al., (1998b) Med. Arch, 52:167–173; Doris et al., (1999) Lancet, 354:1369–1375). Disability and suffering from a mood disorder even extends beyond the patient to their spouses, children, parents, siblings, and friends, who experience frustration, guilt, anger, financial hardship and, on occasion, physical abuse, all in their attempts to assuage or cope with the depressed person's suffering. A large portion of health care expenditures go to treating individuals having depression. Paradoxically, much of treatment does not address the mood disorder because individuals try to seek treatment for other problems in order to avoid the stigma associated with having a mood disorder diagnosis. Consequently, patients with depression undergo extensive and expensive diagnostic procedures of no benefit while their mood disorder goes undiagnosed.

The genetics of mood disorders appears complex and it has been proposed that anticipation and/or genomic imprinting of candidate genes contribute to the observed mode of inheritance (Grigoroiu-Serbanescu (1992) Rom J Neural Psychiatry, 30,265–277. Grigoroiu-Serbanescu (1995) Acta Psychiatr Scand, 92, 365–370. ; McMahon, et al. (1995) Am J Hum Genet, 56, 1277–1286; Kato, et al. (1996) Am J Med Genet, 67, 546–550; Grigoroiu-Serbanescu, et al.(1997) Br J Psychiatry, 170, 162–166). Researchers have identified genes generally involved in neurodegenerative disease such as genes of serotonergic, catecholaminergic or GABAergic neurotransmitter systems as well as the genes of the glutamate receptor system. Despite these intensive research efforts, the specific genes involved in mood disorder pathology remain to be identified.

Thus, it would be useful to identify the genes involved in mood disorders so as to improve diagnosis and therapy. The present invention addresses these needs and provide related advantages as well.

SUMMARY OF THE INVENTION

In accordance with the present invention, there are provided methods of determining predisposition of a subject to a mood disorder by determining the presence of a kainate receptor subunit GluR7 allelic genotype or allelic phenotype. In one embodiment, the allelic genotype is homozygosity for a thymine containing nucleotide at position 928 (928T/T) or homozygosity for a guanine containing nucleotide position 928 (928G/G). The T/T homozygosity is associated with recurrent unipolar depressive disorder while the G/G homozygosity is associated with bipolar II depressive disorder. Various approaches for detecting the GluR7 allelic genotype are also described. A GluR7 allelic phenotype resulting from the nucleotide polymorphism at position 928 results in homozygosity for a serine amino acid at amino acid position 310 (310 Ser/Ser) or homozygosity for an alanine at amino acid position 310 (310 Ala/Ala). The present invention also includes detection of other nucleotide bases in the codon that encode either the alanine or serine at position 928.

Also provided is a method of determining predisposition of a subject to a mood disorder for a subject having a T/G heterozygosity at nucleotide position 928 in the GluR7 gene, the method comprising determining in a biological sample of the subject, a predominance in the expression of either the T allele or the G allele. In a specific embodiment, the predominance of one allele over the other is 1.2 fold or greater. Methods for measuring GluR7 allele expression at the mRNA or protein level are also provided.

The present invention also includes a method of treating or preventing a mood disorder effected by abnormal GluR7 receptor subunit activity or function in a subject. The method comprises administering to a subject an effective amount of a compound that modulates GluR7 receptor subunit activity or function.

Also included is a method for identifying such a compound by incubating a cell expressing a GluR7 receptor subunit with a test compound under conditions sufficient to permit the test compound to interact with the cell and comparing the activity or function of said GluR7 receptor subunit when incubated in the presence of the compound with the activity or function of a GluR7 receptor subunit when incubated in the absence of the compound.

Further included are kits for carrying out the methods of the invention.

Still further included are transgenic non-human animals that express a human GluR7 allele.

DETAILED DESCRIPTION OF THE INVENTION

In accordance with the present invention, it has been discovered that particular nucleotide polymorphisms in the kainate receptor subunit GluR7 are associated with a mood disorder. Nucleotide polymorphism at nucleotide base position 928 in the cDNA of the GRIK3 gene (GenBank Accession Number U16127) results in either a T or a G. As disclosed herein, an individual who is homozygous T/T at 928 of GluR7 has a predisposition to recurrent unipolar depressive disorder. In contrast, an individual who is homozygous G/G at 928 of GluR7 has a predisposition to bipolar II depressive disorder. The present invention also includes detection of other nucleotide bases in the codon at position 928 for alanine (GCT, GCC, GCA and GCG) or serine (TCT, TCC, TCA and TCG, AGT or AGC). Furthermore, individuals heterozygous at nucleotide position 928 (T/G) have a predisposition to recurrent unipolar depressive disorder or predisposition to bipolar II depressive disorder if their expression of the T allele predominates over the G allele or vice versa, respectively. Thus, the present invention provides a method of determining predisposition of a subject to a mood disorder. In its broadest form, the method comprises determining the presence of a kainate receptor subunit GluR7 allelic genotype or allelic phenotype in a biological sample of an individual.

As used herein, "predisposition" refers to a condition of susceptibility to a disorder or disease. An individual with a predisposition to a disorder is more likely than an individual without the predisposition to develop the disorder. Accordingly, an individual predisposed to a mood disorder is more likely to develop a mood disorder than an individual without such a predisposition.

As used herein, "mood disorder" refers to a psychiatric disorder involving disturbances in thinking, emotion, or behavior. Mood disorders are psychiatric illnesses in which emotional disturbances, also called affective disorders, include prolonged periods of excessive depression or elation (mania). Chronic and recurring depressions are termed unipolar depressive disorders. Bipolar disorder, in which periods of depression alternate with periods of mania (or with periods of less severe mania known as hypomania) affects nearly 2 percent of the population. Manic-depressive illness usually begins with depression and includes at least one period of mania at some time during the illness. Episodes of depression typically last 3 to 6 months. In the most severe form of the illness, called bipolar I disorder, depression alternates with intense mania. In the less severe form, called bipolar II disorder, short depressive episodes alternate with hypomania. Symptoms of bipolar II disorder often recur in certain seasons, for example, depression occurs in the fall and winter, and brief excitement occurs in the spring or summer. In an even milder form of manic-depressive illness, called cyclothymic disorder, periods of elation and depression are less severe, typically last for only a few days, and recur fairly often at irregular intervals. Although cyclothymic disorder may ultimately evolve into manic-depressive illness, in many people cyclothymic disorder never leads to major depression or mania.

As used herein, "polymorphism" refers to the occurrence of two or more genetically determined variant forms (alleles) of a particular nucleic acid at a frequency where the rarer (or rarest) form could not be maintained by recurrent mutation alone. An allele such as a single nucleotide polymorphism ("SNP") results from a single base difference between related genes at the same locus. Exemplary nucleotide polymorphisms include bi-allelic polymorphisms such as thymine/thymine (T/T) homozygosity and thymine/guanine (T/G) heterozygosity at position 928 of the GluR7 gene. SNP's may be detectable at the protein level is the nucleotide change is in the coding sequence and encodes a different amino acid residue.

The human kainate type receptor subunit GluR7 is encoded by the GRIK3 (Glutamate Receptor Ionotropic Kainate 3) gene (GenBank under Accession Number U16127), which has been mapped to chromosome 1 at location 1p34-33. GRIK3 encodes a protein about 919 amino acids in length which includes several potential transmembrane domains (amino acid positions 247 to 267, 313 to 333, 564 to 584, 637 to 657 and 821 to 841). The function of the GluR7 receptor in the central nervous system (CNS) is unknown. GluR7 receptor mRNA has been detected in the deep cortical layers (layer IV, V and VI), dentate gyrus, entorhinal cortex, cingulate cortex, anterior amygdaloid area, reticular thalamic nucleus, mammillary bodies in the hypothalamus, and stellate/basket cells in the molecular layer of the mouse/rat brain (Nutt et al., (1994) supra; Lomeli, et al. (1992) *FEBS Lett,* 307, 139–143; Bettler, et al. (1992) Neuron, 8, 257–265). Bishoff et al, (1977) *J Comp Neural,* 379, 541–562) detected GluR7 receptor mRNA expression in dopaminergic neurons in the mouse basal ganglia and ventral mesencephalon.

The GRIK3 gene contains several polymorphisms. A single nucleotide polymorphism is located at nucleotide position 928 in the GRIK3 cDNA where the nucleotide base is thymine or guanine. The nucleotide polymorphism results in an alteration in the extracellular region of the GluR7 receptor subunit at amino acid 310. When nucleotide 928 is thymine, the protein encoded has a serine residue at position 310; when nucleotide 928 is guanine, the protein encoded has an alanine at position 310. Another single nucleotide polymorphism results in the replacement of arginine with lysine at amino acid 303.

The ionotropic glutamate receptors, which include kainate receptors, the α-amino-3-hydroxy-5-methyl-4-isoxazolepropionate (AMPA) receptors and the N-methyl-D-aspartate (NMDA) receptors, mediate fast excitatory synaptic transmission in the mammalian central nervous system (CNS) and play a central role in learning and memory (Hollmann and Heinemann, (1994) Ann. Rev. Neurosci. 17:31–108; Sprengel and Seeburg, (1995) In: *Ligand- and Voltage-gated ion channels,* North (ed.), CRC Press, Boca Raton, pp 213–263; Dingledine et al., (1999) *Pharmacol Rev.* 51:7–61). Calcium influx through ionotropic glutamate receptors modulates numerous transcriptional, translational, and post-translational mechanisms that affect the fate of individual cells, brain regions, and ultimately the whole nervous system. GluR7 is a low-affinity subunit that forms homomeric and heteromeric kainate receptors (Frerking and Nicoll (2000) *Curr. Opin. Neurobio.,* 10:342–351; Chittajallu et al., (1999) *TIPs,* 20:26–35). GluR7 receptors contain a glutamine at the glutamine/arginine (Q/R) site and do not undergo RNA editing, suggesting that this receptor subunit remains calcium permeable.

GluR7 nucleotide polymorphisms associated with predisposition to a mood disorder can be detected by any of a variety of methods known to those of skill in the art. These include any of the large number of methods for detecting SNPs, for example, by restriction fragment length polymorphism (RFLP) analysis. Restriction fragment length polymorphism analysis is a means of detecting nucleotide polymorphisms by restricting or enzymatically cutting a sequence of nucleic acid suspected of containing a polymorphism. The detection method relies on the differential specificity of restriction enzymes (exonucleases and endonucleases) for nucleic acid sequences. For example, one endonuclease, SmaI, upon recognition of the nucleotide sequence -C C C G G G- contained within a DNA sequence, cuts the DNA sequence between the adjacent C (cytosine) and G (guanine). A sequence containing a polymorphism in the recognition sequence will not be recognized by the same restriction nuclease and will be not be restricted. For example, when the recognition sequence contains a single nucleotide polymorphism such that a guanine base is replaced by a thymine base, i.e., the sequence is -C C C G G T-, no SmaI restriction occurs. Thus, an analysis of the nucleic acid fragments generated by contacting a nucleic acid with one or more restriction enzymes allows a determination of the presence of a polymorphism in the nucleic acid sequence. Details for performing RFLP detection can be found, for example, in Sambrook et al., CSH, Press, Cold Spring Harbor, 1989.

Other well known approaches for SNP detection useful herein involve hybridization of an oligonucleotide probe complementary to the site containing the polymorphism to be detected. These analyses are typically performed in conjunction with amplification of the DNA being tested, for example, by the polymerase chain reaction (PCR) (see, e.g. U.S. Pat. Nos. 4,683,195 and 4,683,202), such as anchor PCR or RACE PCR. In a merely illustrative embodiment, the method includes the steps of (i) collecting a sample of cells from a patient, (ii) isolating nucleic acid (e.g., genomic, mRNA or both) from the cells of the sample, (iii) contacting the nucleic acid sample with one or more primers which specifically hybridize to a T928 or a G928 containing GluR7 gene or mRNA under conditions such that hybridization and amplification of the particular allele (if present) occurs, and (iv) detecting the presence or absence of an amplification product. The product also optionally may be compared with the result of amplifying a control sample. It is anticipated that PCR, LCR or any other amplification procedure (e.g. self sustained sequence replication (Guatelli, J. C. et al., 1990, Proc. Natl. Acad. Sci. USA 87:1874–1878), transcriptional amplification system (Kwoh, D. Y. et al., 1989, Proc. Natl. Acad. Sci. USA 86:1173–1177), or Q-Beta Replicase (Lizardi, P. M. et al., 1988, Bio/Technology 6:1197)), may be used as a preliminary step to increase the amount of sample on which can be performed, any of the techniques for detecting mutations described herein.

"Genetic bit analysis" (Goelet, P. et al., PCT Appln. No. WO 92/15712) is an SNP detection method involving hybridization of an oligonucleotide probe complementary to the site containing the polymorphism to be detected. In this method, an oligonucleotide complementary to a DNA sequence immediately 3' to the SNP site is added along with a DNA polymerase and a labeled dideoxynucleoside triphosphate corresponding to the SNP desired to be detected. The label is typically a fluorescent dye or a radionucleotide. The presence of the label in the oligonucleotide probe following denaturation and chain elongation indicates that the SNP is present (see Nikiforov et al., Nucleic Acids Research 22:4167–4175 (1994)). The method of Goelet, P. et al. is preferably a heterogeneous phase assay, in which the primer or the target molecule is immobilized to a solid phase (in contrast to the method of Cohen et al., French Patent No. 2,650,840; PCT Appln. No. WO91/02087)). Other suitable primer-guided nucleotide incorporation procedures for assaying polymorphic sites in DNA have been described (see Komher, J. S. et al., Nucl. Acids. Res. 17:7779–7784 (1989); Sokolov, B. P., Nucl. Acids Res. 18:3671 (1990); Syvanen, A.-C., et al., Genomics 8:684–692 (1990); Kuppuswamy, M. N. et al., Proc. Natl. Acad. Sci. (U.S.A.) 88:1143–1147 (1991); Prezant, T. R. et al., Hum. Mutat. 1:159–164 (1992); Ugozzoli, L. et al., GATA 9:107–112 (1992); Nyren, P. et al., Anal. Biochem. 208:171–175 (1993)).

Fluorescence energy transfer dyes also can be used in combination with a genetic bit type assay, essentially as described in U.S. Pat. No. 5,945,283 to Kwok, et al. In this method, the oligonucleotide probe is labeled with a single fluorophore and is allowed to hybridize to DNA with the target SNP site as above. The labeled dideoxynucleoside triphosphate representing the SNP to be detected is labeled with a suitable fluorophore that can achieve fluorescence energy transfer with the dye on the probe. Primer extension with a DNA polymerase is performed and detection of fluorescence resonance energy transfer upon denaturation indicates the dideoxynucleoside triphosphate representing the SNP and carrying the second fluorophore had been incorporated. Other variations of the genetic bit assay which are known in the art also are included within the meaning of this term.

As used herein, the "oligonucleotide ligation assay" involves hybridization of a DNA sequence to two oligonucleotide probes, one of which is labeled. One of the probes hybridizes to the nucleotides immediately contiguous to a target nucleotide and a second, allele-specific probe hybridizes to the target nucleotide and the immediately contiguous nucleotides on the opposite side of the first probe. Ligase is added and the size of the labeled oligonucleotide is determined. If the DNA tested contained the allele detected by the allele specific probe, then both probes would be fully hybridized at the site of the SNP, allowing the probes to be ligated into a higher molecular weight species. However, if the DNA tested did not contain the allele detected by the allele specific probe, then the end nucleotide of the allele specific probe closest to the end of the other probe would not be ligated and higher molecular weight labeled nucleic acid would not be present (see Nickerson et al., Proc Natl Acad Sci 87:8923–8927, 1990; U.S. Pat. Nos. 4,883,750, 4,988,617 and 5,242,794). If one of the oligonucleotides is linked to a separation marker, e.g., biotinylated, and the other is detectably labeled, ligation then permits the labeled oligonucleotide to be recovered using avidin, or another biotin ligand. Nickerson, D. A. et al. have described a nucleic acid detection assay that combines attributes of PCR and OLA (Nickerson, D. A. et al., Proc. Natl. Acad. Sci. (U.S.A.) 87:8923–8927 (1990). In this method, PCR is used to achieve the exponential amplification of target DNA, which is then detected using OLA.

Several techniques based on this OLA method have been developed and can be used to detect specific allelic variants of a polymorphic region of the GluR7 gene or mRNA. For example, U.S. Pat. No. 5,593,826 discloses an OLA using an oligonucleotide having 3' -amino group and a 5' -phosphorylated oligonucleotide to form a conjugate having a phosphoramidate linkage. In another variation of OLA described in Tobe et al. ((1996) Nucleic Acids Res 24: 3728), OLA combined with PCR permits typing of two alleles in a single microtiter well. By marking each of the allele-specific primers with a unique hapten, i.e. digoxigenin and fluorescein, each OLA reaction can be detected by using hapten specific antibodies that are labeled with different enzyme reporters, alkaline phosphatase or horseradish peroxidase. This system permits the detection of the two alleles using a high throughput format that leads to the production of two different colors. Other variations of the oligonucleotide ligation assay which are known in the art also are included within the meaning of this term.

The oligonucleotide ligation assay may be combined with amplification in a format known as "ligase chain reaction" (see e.g., U.S. Pat. No. 5,912,148 to Eggerding; Barany, Proc. Natl. Acad. Sci. USA, 88:189–193, 1991; Fang et al., Human Mutation, 6:144–151, 1995; Landegran et al. (1988) Science 241:1077–1080; and Nakazawa et al. (1994) PNAS 91:360–364). Other variations of the "ligase chain reaction" assay which are known in the art also are included within the meaning of this tern.

SNPs also may be detected by the "cleaved amplified modified polymorphic sequence" (CMPS) detection method as described in U.S. Pat. No. 6,110,709 to Ausubel et al. In brief, a nucleic acid molecule containing a SNP is mutagenized during PCR amplification to create a restriction endonuclease recognition site which includes the SNP. The resulting PCR product is digested with the corresponding restriction endonuclease, and the restriction endonuclease-treated products are analyzed for cleavage such as in a rapid high through-put assay. These and many other known methods for detection of SNPs, well known to the ordinary skilled artisan, are intended to be used in the methods of the invention.

GluR7 SNPs also may be detected indirectly though linkage disequilibrium mapping as described in McCarthy et al., Nature Biotechnology, 18:505 (2000).

It should be understood that in the above methods, the nucleic acid containing sample of the individual can be analyzed for any of a variety of GluR7 SNPs, including the T928 SNP and the G928 SNP. If both alleles at nucleotide position 928 are analyzed, one can determine if the individual is homozygous for T/T or G/G, or heterozygous T/G.

A preferred detection method is allele specific hybridization using probes overlapping the nucleotide position 928 and having about 5, 10, 20, 25, or 30 nucleotides around position 928. In a preferred embodiment of the invention, several probes capable of hybridizing specifically to the position 928 allelic variants are attached to a solid phase support, e.g., a "chip". Oligonucleotides can be bound to a solid support by a variety of processes, including lithography. For example a chip can hold up to about 250,000 oligonucleotides. Mutation detection analysis using these chips comprising oligonucleotides, also termed "DNA probe arrays" is described e.g., in Cronin et al. (1996) Human Mutation 7:244. In one embodiment, a chip comprises probes for the allelic variants of human GluR7 in an array. The solid phase support is then contacted with a test nucleic acid from an individual and hybridization to the specific probes is detected. Accordingly, the identity of numerous allelic variants of one human GluR7 can be identified in a simple hybridization experiment.

In yet another embodiment, any of a variety of sequencing reactions known in the art can be used to directly sequence the human GluR7 gene and detect the nucleotide at position 928 Exemplary sequencing reactions include those based on techniques developed by Maxim and Gilbert (Proc. Natl Acad Sci USA (1977) 74:560) or Sanger (Sanger et al (1977) Proc. Nat. Acad. Sci 74:5463). It is also contemplated that any of a variety of automated sequencing procedures may be utilized when performing the subject assays (Biotechniques (1995) 19:448), including sequencing by mass spectrometry (see, for example PCT publication WO 94/16101; Cohen et al. (1996) Adv Chromatogr 36:127–162; and Griffin et al. (1993) Appl Biochem Biotechnol 38:147–159). In a further embodiment, protection the identification of the base at position 928 of the GluR7 gene or mRNA may be determined using an oligo probe in conjunction with a cleavage agent (such as a nuclease, hydroxylamine or osmium tetroxide and with piperidine) such as is known can be used to detect mismatched bases in RNA/RNA or RNA/DNA or DNA/DNA heteroduplexes (Myers, et al. (1985) Science 230:1242). The double-stranded duplexes are treated with an agent which cleaves single-stranded regions of the duplex such as which will exist due to base pair mismatches between the control and sample strands. For instance, RNA/DNA duplexes can be treated with RNase and DNA/DNA hybrids treated with S1 nuclease to enzymatically digest the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material may be separated by size on denaturing polyacrylamide gels to determine the site of mutation. See, for example, Cotton et al (1988) Proc. Natl Acad Sci USA 85:4397; Saleeba et al (1992) Methods Enzymol. 217:286–295. In a preferred embodiment, a control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting the base at position 928 in the gene or mRNA encoding human GluR7. For example, the mutY enzyme of E. coli cleaves A at G/A mismatches and the thymidine DNA glycosylase from HeLa cells cleaves T at G/T mismatches (Hsu et al. (1994) Carcinogenesis 15:1657–1662). According to an exemplary embodiment, a probe based on the GluR7 sequence that hybrides at position 928, is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility can be used to identify the allelic variant of GluR7. For example, single strand conformation polymorphism (SSCP) may be used to detect differences in electrophoretic mobility between different allelic variants similar to its use to detect mutant and wild type nucleic acids (Orita et al. (1989) Proc Natl. Acad. Sci USA 86:2766, see also Cotton (1993) Mutat Res 285:125–144; and Hayashi (1992) Genet Anal Tech Appl 9:73–79). For example, a single-stranded DNA fragment of the sample and a nucleic acid that is homozygous T/T 928 or G/G 928 are denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) Trends Genet 7:5).

Examples of other techniques for detecting the T 928 or G 928 allelic variant in GluR7 include, but are not limited to, selective oligonucleotide hybridization, selective amplification, or selective primer extension. For example, oligonucleotide primers may be prepared in which the known nucleotide difference in allelic variants is placed centrally and then hybridized to target DNA under conditions which permit hybridization only if a perfect match is found (Saiki et al. (1986) Nature 324:163); Saiki et al (1989) Proc. Natl Acad. Sci USA 86:6230).

Alternatively, allele specific amplification technology which depends on selective PCR amplification may be used in conjunction with the instant invention. Oligonucleotides used as primers for specific amplification may carry the polymorphic region of interest in the center of the molecule (so that amplification depends on differential hybridization) (Gibbs et al (1989) Nucleic Acids Res. 17:2437–2448) or at the extreme 3' end of one primer where, under appropriate conditions, mismatch can prevent, or reduce polymerase extension (Prossner (1993) Tibtech 11:238. In addition it may be desirable to introduce a novel restriction site in the region of the mutation to create cleavage-based detection (Gasparini et al (1992) Mol. Cell Probes 6:1). It is anticipated that in certain embodiments amplification may also be performed using Taq ligase for amplification (Barany (1991) Proc. Natl. Acad. Sci USA 88:189). In such cases, ligation will occur only if there is a perfect match at the 3' end of the 5' sequence making it possible to detect the presence of a known mutation at a specific site by looking for the presence or absence of amplification.

In another embodiment, the single base polymorphism can be detected by using a specialized exonuclease-resistant nucleotide, as disclosed, e.g., in Mundy, C. R. (U.S. Pat. No. 4,656,127). According to the method, a primer complementary to the allelic sequence immediately 3' to the polymorphic site is permitted to hybridize to a target molecule obtained from a particular animal or human. If the polymorphic site on the target molecule contains a nucleotide that is complementary to the particular exonuclease-resistant nucleotide derivative present, then that derivative will be incorporated onto the end of the hybridized primer. Such incorporation renders the primer resistant to exonuclease, and thereby permits its detection. Since the identity of the exonuclease-resistant derivative of the sample is known, a finding that the primer has become resistant to exonucleases reveals that the nucleotide present in the polymorphic site of the target molecule was complementary to that of the nucleotide derivative used in the reaction. This method has the advantage that it does not require the determination of large amounts of extraneous sequence data.

In another embodiment of the invention, a solution-based method is used for determining the identity of the nucleotide of a polymorphic site. Cohen, D. et al. (French Patent 2,650,840; PCT Appln. No. WO91/02087). As in U.S. Pat. No. 4,656,127, a primer is employed that is complementary to allelic sequences immediately 3' to a polymorphic site. The method determines the identity of the nucleotide of that site using labeled dideoxynucleotide derivatives, which, if complementary to the nucleotide of the polymorphic site will become incorporated onto the terminus of the primer.

Samples from an individual may be from any tissue or cell and may include a bodily fluid such as blood. Alternatively, nucleic acid tests can be performed on dry samples (e.g. hair or skin). The sample may contain genomic DNA, cDNA or RNA. Methods of preparing genomic DNA or cDNA and RNA are well known in the art (See Sambrook, supra, 1989). For prenatal diagnosis, fetal nucleic acid samples can be obtained from maternal blood as described in International Patent Application No. WO91/07660 to Bianchi. Alternatively, amniocytes or chorionic villi may be obtained for performing prenatal testing.

Diagnostic procedures may also be performed in situ directly upon tissue sections (fixed and/or frozen) of tissue obtained from biopsies or resections. Nucleic acid reagents may be used as probes and/or primers for such in situ procedures (see, for example, Nuovo, G. J., 1992, PCR in situ hybridization: protocols and applications, Raven Press, N.Y.).

As already described, the nucleotide polymorphisms of GluR7 at nucleotide position 928 result in a different amino acid at the protein level. Thus, when nucleotide 928 is thymine, the GluR7 encoded protein has a serine residue at position 310; when nucleotide 928 is a guanine, the GluR7 encoded has an alanine at position 310. Thus, it will be readily appreciated that any of a variety of protein detecting methods can be applied to detect the particular SNP resulting in serine or alanine at position 310 in human GluR7. Such methods may include amino acid sequencing, immunodetetion, chromatography such as high pressure liquid chromatography, peptide mapping, and the like.

Monoclonal antibodies or polyclonal sera specific to serine at 310 of GluR7 or alanine at 310 of GluR7 may be prepared by immunization with synthetic peptides using immunization methods well known in the art (see Harlow and Lane, for example, (Harlow, E. and Lane, D., 1988, "Antibodies: A Laboratory Manual", Cold Spring Harbor Laboratory Press, Cold Spring Harbor, N.Y.). In the case of polyclonal sera, absorption with the other of the SNPs may be used to reduce cross reactivity. Immunodetection of the particular GluR7 allelic phenotype can be accomplished by any of a variety of methods well known in the art, including Western blot analysis, ELISA, immunofluorescence and the like (see Harlow and Lane, supra).

For example, techniques employing a fluorescently labeled antibody (see below) may be coupled with light microscopy, flow cytometry, or fluorimetry. The antibodies (or fragments thereof) may, additionally, be employed histologically, as in immunofluorescence or immunoelectron microscopy, for in situ detection of GluR7 allelic polypeptides. In situ detection may be accomplished by removing a histological specimen from a patient, and applying thereto a labeled antibody of the present invention. The antibody (or fragment) is preferably applied by overlaying the labeled antibody (or fragment) onto a biological sample. Through the use of such a procedure, it is possible to determine not only the presence of the GluR7 allelic polypeptide present, but also its distribution in the examined tissue. Using the present invention, one of ordinary skill will readily perceive that any of a wide variety of histological methods (such as staining procedures) can be modified in order to achieve such in situ detection.

Often a solid phase support or carrier is used as a support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will know many other suitable carriers for binding antibody or antigen, or will be able to ascertain the same by use of routine experimentation.

Antibody reagents may be labeled to assist detection of binding. Labeling via linkage to an enzyme is useful or enzyme immunoassay (EIA) (Voller, "The Enzyme Linked Immunosorbent Assay (ELISA)", Diagnostic Horizons 2:1–7, 1978, Microbiological Associates Quarterly Publication, Walkersville, Md.; Voller, et al., J. Clin. Pathol. 31:507–520 (1978); Butler, Meth. Enzymol. 73:482–523 (1981); Maggio, (ed.) Enzyme Immunoassay, CRC Press, Boca Raton, Fla., 1980; Ishikawa, et al., (eds.) Enzyme Immunoassay, Kgaku Shoin, Tokyo, 1981). The enzyme which is bound to the antibody will react with an appropriate substrate, preferably a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol ehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colorimetric methods which employ a chromogenic substrate for the enzyme. Detection may also be accomplished by visual comparison of the extent of enzymatic reaction of a substrate in comparison with similarly prepared standards.

Detection also may be accomplished using any of a variety of other immunoassays. For example, by radioactively labeling the antibodies or antibody fragments, it is possible to detect the GluR7 allelic protein through the use of a radioimmunoassay (RIA) (see, for example, Weintraub, B., Principles of Radioimmunoassays, Seventh Training Course on Radioligand Assay Techniques, The Endocrine Society, March, 1986, which is incorporated by reference herein). The radioactive isotope can be detected by such means as the use of a gamma counter or a scintillation counter or by autoradiography.

Antibody may be coupled with a fluorescent compound for the methods discussed above. When the fluorescently labeled antibody is exposed to light of the proper wave length, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine.

Antibody also may be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA).

A chemiluminescent compound may be conjugated to an antibody for assisting in detection. Presence of the chemiluminescent-tagged antibody is determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody. Bioluminescence is a type of chemiluminescence found in biological systems in, which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

The present inventive methods of determining predisposition also may be used in genetic counseling of individuals prior to the decision to conceive a child. Also, application of methods for detecting the GluR7 SNPs as described herein can be applied to the parents of an individual with a mood disorder to determine from which parent the GluR7 SNP was inherited. The transmission of the polymorphism refers to the distribution of a GluR7 polymorphic allele from parent to offspring. When a parent is heterozygous for a polymorphism, for example thymine/guanine (T/G) at position 928, the likelihood that the thymine allele is transmitted is usually the same as the likelihood that the guanine allele is transmitted to the offspring. A genetic locus that is linked to another locus shows equal allelic transmission.

Family-based association studies can reveal if a gene or closely linked chromosomal locus is involved in a disease or disorder. One such type of study, a transmission disequilibrium test (TDT) detects the linkage of a genetic marker and a disease locus in the presence of linkage disequilibrium of the two loci (Spielman et al. (1993) *Am. J. Human Genetics*, 52:506–516; Spielman and Ewens (1996) *Am. J. Human Genetics*, 59:983–989; Ewens and Spielman (1998) *Am. J. Human Genetics*, 62:450–458; Sun et al. (1999) *Am. J. Epidemiol.* 150:97–104). Preferential transmission of an allele containing a genetic marker (rather than an allele not containing the genetic marker) from heterozyous parent(s) to an offspring indicates a predisposition in the offspring for the disease or disorder linked to the genetic marker (See Example 2 for details.).

As described herein, predisposition to a mood disorder can be determined in T/G 928 heterozygous individuals by determining if the T or the G allele is predominantly expressed over that of the other. In a preferred embodiment, the expression of one allele over the other is 1.2 fold or greater. The expression level for each allele can be determined using GluR7 encoding mRNA or GluR7 protein. The level of expression of each allele in mRNA can be determined following the methods in Example 2. In this case, the alleles can be detected using a cycled primer extension assay with dideoxy terminators, as described in Schiffer and Heinemann, (1999) (*Anal Biochem,* 276: 257–260). Labeled primers extended by this approach can be separated by electrophoresis, the gels dried and image analyzed to quantify the relative amount of each allele in the analyzed DNA fragment fraction. Relative expression of each GluR7 allele is then determined by calculating a ratio between the detected amounts of each allele. Other methods can be used including slot blotting, Northern blotting, and the like. Likewise, the level of each allele can be determined by detecting each GluR7 protein allele using the protein detecting methods described above.

The present invention also provides a kit for determining predisposition of a subject to a mood disorder, the kit comprising at least one specific reagent useful in detection of a kainate receptor subunit GluR7 polymorphism associated with a mood disorder. The "specific reagent" as used herein is any chemical substance that directly or indirectly can be used to detect the GluR7 allele, either at the nucleotide level or at the protein level. Thus, a specific reagent is an oligonucleotide specific for either the T928 or G928 alleles. A specific reagent also is an antibody with binding specificity for GluR7 having a serine at position 310 or for GluR7 having an alanine at position 310, but not both. The specific reagent may be detectably labeled as described above. As is well known in the art, the kit can include various buffers and other reagents needed in the particular assay format contemplated.

The present invention also provides a method of treating or preventing a mood disorder effected by abnormal GluR7 receptor subunit activity or function in a subject, the method comprising administering to said subject an effective amount of a compound that modulates GluR7 receptor subunit activity or function. In a preferred embodiment, the compound modifies the activity or function of the GluR7 receptor subunit having a thymine at nucleotide position 928 of the human GluR7 receptor subunit.

The term "modulate" as used in modulating GluR7 receptor subunit activity or function, envisions the suppression of a GluR7 receptor subunit activity or expression when GluR7 receptor subunit is overexpressed or has an increased activity as compared to a control. The term "modulate" also includes the augmentation of the expression of a GluR7 receptor subunit when it is underexpressed or has a decreased activity as compared to a control. The term "compound" as used herein describes any molecule, e.g., protein, nucleic acid, peptide, peptidomimetic, polypeptide, pharmaceutical, biological agent, antibody, neurotropic agent or combinatorial library with the capability of altering the expression or activity of a GluR7 receptor subunit.

As used herein, "treating" refers to inhibiting or arresting the development of a disease, disorder or condition and/or causing the reduction, remission, or regression of a disease, disorder or condition. Those of skill in the art will understand that various methodologies and assays may be used to assess the development of a disease, disorder or condition, and similarly, various methodologies and assays may be used to assess the reduction, remission or regression of a disease, disorder or condition. As used herein, the phrase "preventing disease conditions" refers to preventing a disease, disorder or condition from occurring in a subject who may be at risk for the disease, but has not yet been diagnosed as having the disease.

As used herein, a "subject in need" refers to an individual who has been diagnosed with a disease, disorder, or condition, or who is predisposed for a disease, disorder or condition. Those of skill in the art will understand that a variety of methods may be used to determine a subject at risk for a disease, and that whether a subject is at risk for a disease will depend on a variety of factors known to those of skill in the art, including genetic make-up of the subject, age, body weight, sex, diet, general health, occupation, exposure to environmental conditions, marital status, and the like, of the subject.

As used herein, "administering" refers to means for providing a compound that modulates a GluR7 receptor subunit activity or function to a patient, using any suitable route, e.g. oral, sublingual intravenous, subcutaneous, transcutaneous, intramuscular, intracutaneous, intrathecal, epidural, intraoccular, intracranial, inhalation, rectal, vaginal, and the like administration. Administration of compounds in the form of creams, lotions, tablets, capsules, pellets, dispersible powders, granules, suppositories, syrups, elixirs, lozenges, injectable solutions, sterile aqueous or non-aqueous solutions, suspensions or emulsions, patches, and the like, is also contemplated. The active ingredients may be compounded with non-toxic, pharmaceutically acceptable carriers including, glucose, lactose, gum acacia, gelatin, mannitol, starch paste, magnesium trisilicate, talc, corn starch, keratin, colloidal silica, potato starch, urea, dextrans, and the like.

As employed herein, the phrase "an effective amount", when used in reference to invention methods employing compounds that modulate GluR7 receptor subunit activity or function, refers to a dose of compound sufficient to provide circulating concentrations high enough to impart a beneficial effect on the recipient thereof. The specific therapeutically effective dose level for any particular patient will depend upon a variety of factors including the disorder being treated, the severity of the disorder, the activity of the specific compound used, the route of administration, the rate of clearance of the specific compound, the duration of treatment, the drugs used in combination or coincident with the specific compound, the age, body weight, sex, diet and general health of the patient, and like factors well known in the medical arts and sciences. Dosage levels typically fall in the range of about 0.001 up to 100 mg/kg/day; with levels in the range of about 0.05 up to 10 mg/kg/day being preferred.

When a disorder is associated with the decreased expression or activity of a GluR7 receptor subunit, nucleic acid sequences that encode a GluR7 receptor subunit can be used. Expression vectors that encode a particular GluR7 allele for expression in vitro or in vivo may be delivered to cells in an individual by any of a variety of gene delivery methods. Alternatively, an agent that increases the expression of a polynucleotide encoding GluR7 receptor subunit or an agent that increases the activity of GluR7 receptor subunit polypeptide can be used.

Viral expression vectors can be particularly useful for introducing a GluR7 polynucleotide into a cell. The host cell can be a cell in a subject, a cell in vivo, or a cell ex vivo (see, for example U.S. Pat. No. 5,399,346). Viral vectors provide the advantage that they can infect host cells with relatively high efficiency and can infect specific cell types. Viral vectors can be particularly useful for introducing a polynucleotide useful in performing a method of the invention into a target cell. Viral vectors have been developed for use in particular host systems, particularly mammalian systems and include, for example, retroviral vectors, other lentivirus vectors such as those based on the human immunodeficiency virus (HIV), adenovirus vectors, adeno-associated virus vectors, herpesvirus vectors, vaccinia virus vectors, and the like (see Miller and Rosman, *BioTechniques* 7:980–990, 1992; Anderson et al., *Nature* 392:25–30 Suppl., 1998; Verma and Somia, *Nature* 389:239–242, 1997; Wilson, *New Engl. J. Med.* 334:1185–1187(1996)).

When retroviruses, for example, are used for polynucleotide transfer, replication competent retroviruses theoretically can develop due to recombination of retroviral vector and viral gene sequences in the packaging cell line utilized to produce the retroviral vector. Packaging cell lines in which the production of replication competent virus by recombination has been reduced or eliminated can be used to minimize the likelihood that a replication competent retrovirus will be produced. All retroviral vector supernatants used to infect cells are screened for replication competent virus by standard assays such as PCR and reverse transcriptase assays. Retroviral vectors allow for integration of a heterologous gene into a host cell genome, which allows for the gene to be passed to daughter cells following cell division.

A polynucleotide, which may be contained in a vector, can be introduced into a cell by any of a variety of methods known in the art (Sambrook et al., *Molecular Cloning: A laboratory manual* (Cold Spring Harbor Laboratory Press 1989); Ausubel et al., *Current Protocols in Molecular Biology,* John Wiley and Sons, Baltimore, Md. (1987, and supplements through 1995)). Such methods include, for example, transfection, lipofection, microinjection, electroporation and, with viral vectors, infection; and can include the use of liposomes, microemulsions or the like, which can facilitate introduction of the polynucleotide into the cell and can protect the polynucleotide from degradation prior to its introduction into the cell. The selection of a particular method will depend, for example, on the cell into which the polynucleotide is to be introduced, as well as whether the cell is isolated in culture, or is in a tissue or organ in culture or in situ.

A polynucleotide sequence encoding a GluR7 allele can be expressed in either prokaryotes, eukaryotes, including plants. Hosts can include microbial, yeast, insect and mammalian organisms. Methods of expressing polynucleotides having eukaryotic or viral sequences in prokaryotes are well known in the art, as are biologically functional viral and plasmid DNA vectors capable of expression and replication in a host. Methods for constructing an expression vector containing a polynucleotide of the invention are well known, as are factors to be considered in selecting transcriptional or translational control signals, including, for example, whether the polynucleotide is to be expressed preferentially in a particular cell type or under particular conditions (see, for example, Sambrook et al, supra, 1989).

Depending on the host cell/vector system utilized, any of a number of suitable transcription and translation elements, including constitutive and inducible promoters, transcription enhancer elements, transcription terminators, and the like, can be used in the expression vector (Bitter et al., *Meth. Enzymol.* 153:516–544, 1987). For example, when cloning in bacterial systems, inducible promoters such as pL of bacteriophage λ, plac, ptrp, ptac (ptrp-lac hybrid promoter) and the like, can be used. When cloning in mammalian cell systems, promoters derived from the genome of mammalian cells, for example, a human or mouse metallothionein promoter, or from mammalian viruses, for example, a retrovirus long terminal repeat, an adenovirus late promoter or a vaccinia virus 7.5K promoter, can be used. Promoters produced by recombinant DNA or synthetic techniques can also be used to provide for transcription of the inserted GDF receptors coding sequence.

Mammalian cell systems which utilize recombinant viruses or viral elements to direct expression can be engineered. For example, when using adenovirus expression vectors, the GluR7 protein coding sequence can be ligated to an adenovirus transcription/translation control complex, e.g., the late promoter and tripartite leader sequence. Alternatively, the vaccinia virus 7.5K promoter can be used (Mackett et al., *Proc. Natl. Acad. Sci., USA* 79:7415–7419, 1982; Mackett et al, *J. Virol.* 49:857–864, 1984; Panicali et al., *Proc. Natl. Acad. Sci., USA* 79:4927–4931, 1982). Particularly useful are bovine papilloma virus vectors, which can replicate as extrachromosomal elements (Sarver et al., *Mol. Cell. Biol.* 1:486, 1981). Shortly after entry of this DNA into mouse cells, the plasmid replicates to about 100 to 200 copies per cell. Transcription of the inserted cDNA yielding a high level of expression may result without integration of the plasmid into the host cell chromosome. These vectors can be used for stable expression by including a selectable marker in the plasmid, such as, for example, the neo gene. Alternatively, the retroviral genome can be modified for use as a vector capable of introducing and directing the expression of a GluR7 protein in the host cells (Cone and Mulligan, *Proc. Natl. Acad. Sci., USA* 81:6349–6353, 1984). High level expression can also be achieved using inducible promoters, including, but not limited to, the metallothionein IIA promoter and heat shock promoters.

Where a disorder is associated with the increased expression of GluR7 receptor subunit, nucleic acid sequences that interfere with the expression of GluR7 receptor subunit can be used. This approach also utilizes, for example, antisense nucleic acid, ribozymes, or triplex agents to block transcription or translation of GluR7 receptor subunit mRNA, either by masking that mRNA with an antisense nucleic acid or triplex agent, or by cleaving it with a ribozyme in disorders associated with increased GluR7 receptor subunit.

A compound that modulates GluR7 receptor subunit activity or function can be identified by incubating a cell expressing a GluR7 receptor subunit with the compound under conditions sufficient to permit the compound to interact with cell; and comparing the activity or function of said GluR7 receptor subunit incubated in the presence of the compound with the activity or function of a GluR7 receptor subunit in the absence of the compound, thereby identifying a compound that modulates GluR7 receptor subunit activity or function.

Measurement of the level (decreased or increased) of "GluR7 receptor subunit activity" during compound selection can be accomplished by hybridization of nucleic acids isolated from a cell of interest with a nucleic acid encoding a GluR7 receptor subunit. Analyses, such as Northern Blot analysis, are utilized to quantitatively measure expression of a GluR7 receptor subunit, such as to measure GluR7 receptor subunit transcripts. Other standard nucleic acid detection techniques are known by those of skill in the art. Detection of altered levels of GluR7 receptor subunit protein can also be accomplished using assays designed to detect GluR7 receptor subunit polypeptide. For example, antibodies or peptides that specifically bind a GluR7 receptor subunit can be utilized. Analyses, such as radioimmune assay or immunohistochemistry, are then used to measure GluR7 receptor subunit, such as to measure protein concentration qualitatively or quantitatively.

Candidate agents for modulating GluR7 activity or function include nucleic acids encoding a GluR7 receptor subunit, or that interfere with expression of GluR7 receptor subunit, such as an antisense nucleic acid, ribozymes, and the like. Candidate agents also encompass numerous chemical classes wherein the agent modulates GluR7 receptor subunit expression or activity. Candidate compounds may be tested on any cell of interest, including but not limited to neuronal cells, glial cells, cardiac cells, bronchial cells, uterine cells, testicular cells, liver cells, renal cells, intestinal cells, cells from the thymus and spleen, placental cells, endothelial cells, endocrine cells including thyroid, parathyroid, pituitary, and the like, smooth muscle cells, skeletal muscle cells, and the like. In a preferred embodiment, the cell is a neuronal cell or a glial cell. The term "incubating" includes conditions which allow contact between the test compound and the cell of interest.

Candidate agents for modulating the level of GluR7 receptor may include antisense nucleic acid sequences capable of reducing GluR7 receptor subunit when overexpressed. Antisense nucleic acids are DNA or RNA molecules that are complementary to at least a portion of a specific mRNA molecule (Weintraub, 1990, *Scientific American*, 262:40). Antisense oligomers of about 15 nucleotides are preferred, since they are easily synthesized and are less likely to cause problems than larger molecules when introduced into the target cell. The use of antisense methods to inhibit the in vitro translation of genes is well known in the art (Marcus-Sakura, 1988, *Anal. Biochem.*, 172:289).

Ribozymes specific for either the T929 or G929 GluR7 alleles may be designed so that delivery of the ribozyme in vivo can be used to reduce the level of expression of the particular GluR7 allele. There are two basic types of ribozymes namely, tetrahymena-type (Hasselhoff, 1988, *Nature*, 334:585) and "hammerhead"-type. Tetrahymena-type ribozymes recognize sequences which are four bases in length, while "hammerhead"-type ribozymes recognize base sequences 11–18 bases in length. The longer the recognition sequence, the greater the likelihood that the sequence will occur exclusively in the target mRNA species. Consequently, hammerhead-type ribozymes are preferable to tetrahymena-type ribozymes for inactivating a specific mRNA species and 18-base recognition sequences are preferable to shorter recognition sequences.

A strategy related to anti-sense, the triplexed strategy, may be used to inhibit the transcription of a gene. Use of an oligonucleotide to stall transcription, referred to as the triplex strategy, involves intercalating the oligomer into double-helical DNA, forming a three-strand helix. Such triplex compounds can be designed to recognize a unique site on a chosen gene (Maher, et al., 1991, *Antisense Res. and Dev.*, 1:227; Helene, 1991, *Anticancer Drug Design*, 6:569).

Agents that modulate the activity of GluR7 may be obtained by molecular modeling. For this purpose, the GluR7 receptor can be recombinantly expressed and crystalized. X-Ray crystalographic analysis is then used to determine the structure of the receptor at the atomic level and such data is used to prepare computer controlled molecular model of the receptor. By comparing the molecular structure of the two alleles of GluR7, one can identify the key difference(s) in the structure and then model binding compounds that will convert one structure shape to the other. Such compounds following toxicity and efficacy testing in vitro and in vivo can ultimately be administered to T/T or G/G homozygous individuals to generate receptor function that is approximates that which exits in a T/G heterozygous individual.

The present invention also includes the preparation of transgenic non-human animals in which their endogenous genes are deleted or inactivated and replaced by a functional human GluR7 gene for either the T928 allele or the G928 allele. Such animals will be characterized in having a mood disorder and, therefore, provide a non-human animal model from which to study disease progression and therapy. A preferred non-human animal for this purpose is a mouse.

A first step in the process is to knockout the endogenous gene encoding the GluR7 receptor, eliminating expression of the GluR7 protein product. This can be achieved by in vitro manipulation of the early embryo or fertilized egg or by using any transgenic technology to disrupt or induce knockout of the GluR7 gene. Disruption can occur by any of a variety of mechanisms well known to those skilled in the art. For example, disruption can be accomplished by inserting a GluR7 transgene comprising a selectable marker sequence. The disruption will results in a disorder of the nervous system as compared to a wild-type animal not having the disruption.

Transgenic animals having a genetic disruption in the GLUR7 gene are models for diseases or disorders associated with mutations in the GLUR7 protein genes. The animal may be essentially any amphibian, reptile, fish, mammal, insect, arthropod, and the like. Preferably, the transgenic animal is mammalian including rats, mice, hamsters, guinea pigs, rabbits, dogs, cats, goats, sheep, pigs, and non-human primates. In addition, invertebrate models, including arthropods, nematodes and insects, may be used for certain applications. The animal models are produced by standard transgenic methods including microinjection, transfection, or by other forms of transformation of embryonic stem cells, zygotes, gametes, and germ line cells with vectors including genomic or cDNA fragments, minigenes, homologous recombination vectors, viral insertion vectors, and the like. Suitable vectors include vaccinia virus, adenovirus, adeno associated virus, retrovirus, liposome transport, neuraltropic viruses, Herpes simplex virus, and the like. The animal models may include transgenic sequences comprising or derived from GLUR7 proteins including normal and mutant sequences, intronic, exonic and untranslated sequences, and sequences encoding subsets of GLUR7 proteins such as functional domains.

The major types of animal models provided include: (1) Animals in which a normal human GLUR7 gene representing a single nucleotide 929 allele has been recombinantly introduced into the genome of the animal as an additional gene, under the regulation of either an exogenous or an endogenous promoter element, and as either a minigene or a large genomic fragment; (2) Animals in which a human GLUR7 929 allele has been recombinantly substituted for one or both copies of the animal's homologous GLUR7 gene by homologous recombination or gene targeting; and/or in which one or both copies of one of the animal's homologous GLUR7 genes have been recombinantly "humanized" by the partial substitution of sequences encoding the human homologue by homologous recombination or gene targeting; (3) Animals in which a human GLUR7 gene has been recombinantly introduced into the genome of the animal as an additional gene, under the regulation of either an exogenous or an endogenous promoter element, and as either a minigene or a large genomic fragment; (4) Animals in which a mutant human GLUR7 gene has been recombinantly substituted for one or both copies of the animal's homologous GLUR7 gene by homologous recombination or gene targeting and, optionally, in which one or both copies of one of the animal's homologous GLUR7 genes have been recombinantly "humanized" by the partial substitution of sequences encoding a mutant human homologue by homologous recombination or gene targeting. (5) Animals in which a mutant version of one of that animal's GLUR7 genes has been recombinantly introduced into the genome of the animal as an additional gene, under the regulation of either an exogenous or an endogenous promoter element, and as either a minigene or a large genomic fragment and in which a mutant version of one of that animal's GLUR7 genes has been recombinantly substituted for one or both copies of the animal's homologous GLUR7 gene by homologous recombination or gene targeting; and (6) "Knock-out" animals in which one or both copies of one of the animal's GLUR7 genes have been inactivated, for example, by partially or completely deleting through homologous recombination or gene targeting, or by the insertion or substitution (e.g. causing frame shifting) by homologous recombination or gene targeting of exogenous sequences, and the like.

A "transgenic" animal can result from cross-breeding two chimeric animals which include exogenous genetic material within cells used in reproduction. Twenty-five percent of the resulting offspring will be transgenic i.e., animals which include the exogenous genetic material within all of their cells in both alleles. 50% of the resulting animals will include the exogenous genetic material within one allele and 25% will include no exogenous genetic material.

In a preferred embodiment of the invention, there is provided a transgenic non-human animal having a transgene that expresses a GLUR7 nucleotide 929 allele encoding polynucleotide chromosomally integrated into the germ cells of the animal. Animals are referred to as "transgenic" when such animal has had a heterologous DNA sequence, or one or more additional DNA sequences normally endogenous to the animal (collectively referred to herein as "transgenes") chromosomally integrated into the germ cells of the animal. The transgenic animal (including its progeny) will also have the transgene fortuitously integrated into the chromosomes of somatic cells.

Various methods to make the transgenic animals of the subject invention can be employed. In one method, an embryo at the pronuclear stage (a "one cell embryo") is harvested from a female and the transgene is microinjected into the embryo, in which case the transgene will be chromosomally integrated into both the germ cells and somatic cells of the resulting mature animal. In another method, embryonic stem cells are isolated and the transgene incorporated therein by electroporation, plasmid transfection or microinjection, followed by reintroduction of the stem cells into the embryo where they colonize and contribute to the germ line. Methods for microinjection of mammalian species is described in U.S. Pat. No. 4,873,191. In yet another method, embryonic cells are infected with a retrovirus containing the transgene whereby the germ cells of the embryo have the transgene chromosomally integrated therein. Various other methods for making transgenic animals are well known to the skilled artisan and can be used herein.

When the animals to be made transgenic are avian, because avian fertilized ova generally go through cell division for the first twenty hours in the oviduct, microinjection into the pronucleus of the fertilized egg is problematic due to the inaccessibility of the pronucleus. Therefore, of the methods to make transgenic animals described generally above, retrovirus infection is preferred for avian species, for example as described in U.S. Pat. No. 5,162,215. If microinjection is to be used with avian species, however, a recently published procedure by Love et al., (Biotechnology, Jan. 12, 1994) can be utilized whereby the embryo is obtained from a sacrificed hen approximately two and one-half hours after the laying of the previous laid egg, the transgene is microinjected into the cytoplasm of the germinal disc and the embryo is cultured in a host shell until maturity. When the animals to be made transgenic are bovine or porcine, microinjection can be hampered by the opacity of the ova thereby making the nuclei difficult to identify by traditional differential interference-contrast microscopy. To overcome this problem, the ova can first be centrifuged to segregate the pronuclei for better visualization.

The non-human animals of the invention are typically murine (e.g., mouse). The transgenic non-human animals of the invention are produced by introducing "transgenes" into the germline of the non-human animal. Embryonal target cells at various developmental stages can be used to introduce transgenes. Different methods are used depending on the stage of development of the embryonal target cell. The zygote is the best target for microinjection. The use of zygotes as a target for gene transfer has a major advantage in that in most cases the injected DNA will be incorporated into the host gene before the first cleavage (Brinster et al., Proc. Natl. Acad. Sci. USA 82:4438–4442, 1985). As a consequence, all cells of the transgenic non-human animal will carry the incorporated transgene. This will in general also be reflected in the efficient transmission of the transgene to offspring of the founder since 50% of the germ cells will harbor the transgene.

In the microinjection method useful in the practice of the subject invention, the transgene is digested and purified free from any vector DNA, e.g., by gel electrophoresis. In one approach, the transgene includes an operatively associated promoter which interacts with cellular proteins involved in transcription, ultimately resulting in constitutive expression. Promoters useful in this regard include those from cytomegalovirus (CMV), Moloney leukemia virus (MLV), and herpes virus, as well as those from the genes encoding metallothionine, skeletal actin, P-enolpyruvate carboxylase (PEPCK), phosphoglycerate (PGK), DHFR, thymidine kinase, and the like. Promoters for viral long terminal repeats (LTRs) such as Rous Sarcoma Virus can also be employed. Constructs useful in plasmid transfection of embryonic stem cells may include additional regulatory elements well known in the art such as enhancer elements to stimulate transcription, splice acceptors, termination and polyadenylation signals, and ribosome binding sites to permit translation.

Retroviral infection can also be used to introduce transgene into a non-human animal, as described above. The developing non-human embryo can be cultured in vitro to the blastocyst stage. During this time, the blastomeres can be targets for retroviral infection (Jaenich, R., Proc. Natl. Acad. Sci USA 73:1260–1264, 1976). Efficient infection of the blastomeres is obtained by enzymatic treatment to remove the zona pellucida (Hogan, et al. (1986) in Manipulating the Mouse Embryo, Cold Spring Harbor Laboratory Press, Cold Spring Harbor, N.Y.). The viral vector system used to introduce the transgene is typically a replication-defective retrovirus carrying the transgene (Jahner, et al, Proc. Natl. Acad. Sci. USA 82:6927–6931, 1985; Van der Putten, et al., Proc. Natl. Acad. Sci USA 82:6148–6152, 1985). Transfection is easily and efficiently obtained by culturing the blastomeres on a monolayer of virus-producing cells (Van der Putten, supra; Stewart, et al, EMBO J. 6:383–388, 1987). Alternatively, infection can be performed at a later stage. Virus or virus-producing cells can be injected into the blastocoel (D. Jahner et al., Nature 298:623–628, 1982). Most of the founders will be mosaic for the transgene since incorporation occurs only in a subset of the cells which formed the transgenic non-human animal. Further, the founder may contain various retroviral insertions of the transgene at different positions in the genome which generally will segregate in the offspring. In addition, it is also possible to introduce transgenes into the germ line, albeit with low efficiency, by intrauterine retroviral infection of the midgestation embryo (D. Jahner et al., supra).

A third type of target cell for transgene introduction is the embryonal stem cell (ES). ES cells are obtained from pre-implantation embryos cultured in vitro and fused with embryos (M. J. Evans et al. Nature 292:154–156, 1981; M. O. Bradley et al., Nature 309: 255–258, 1984; Gossler, et al., Proc. Natl. Acad. Sci USA 83: 9065–9069, 1986; and Robertson et al., Nature 322:445–448, 1986). Transgenes can be efficiently introduced into the ES cells by DNA transfection or by retro virus-mediated transduction. Such transformed ES cells can thereafter be combined with blastocysts from a non-human animal. The ES cells thereafter colonize the embryo and contribute to the germ line of the resulting chimeric animal. (For review see Jaenisch, R., Science 240: 1468–1474, 1988).

The invention will now be described in greater detail by reference to the following non-limiting examples.

EXAMPLES

Example 1

Methods for Genetic Analysis of GluR7

Brain DNA: Rat genomic DNA (#6750-1), rat total RNA (#64060-1), human genomic DNA (#6550-1) or human total RNA (#64020-1) were obtained from Clontech (Palo Alto, Calif.). Genomic DNA and brain total RNA from neuropsychiatric disorder cases were isolated from brain tissue samples kindly provided by the Stanley Foundation at the NAMI Research Institute in Bethesda, Md. The human genomic control DNAs used for the estimation of GluR7 allele frequency and genotype distribution in the group of Caucasian people were obtained from the Alzheimer Disease Research Center at the University of California, San Diego. E. Masliah from the Department of Neurosciences, University California, San Diego, provided all other human brain tissue samples.

GluR7 Primers: GluR7 cDNA was synthesized with human or mouse total RNA using the GluR7 gene specific primers H7.2952 (CTGGCCTGAGAGCCTGCTGGCTTC; SEQ ID NO:1) or M7.1825 (CGGGGGAGCCTGAGAGGCATGTGC; SEQ ID NO:2), respectively. Human genomic DNA fragments covering the T/G site were amplified by using the primer pair H7.830 (CCTACCGCTACTCAGGCGTGAACC; SEQ ID NO:3 ) and H7.430AS (TTCTTCTTTCTGCCTTCTCGGCCTT; SEQ ID NO:4). Genomic polymerase chain reaction (PCR) products containing the C/T site from the mouse GluR7 gene were obtained by using the GluR7 gene specific primer pair M7.GE.E (TCCTTCCTCAATCCCCTGTCTCCG; SEQ ID NO:5) and M7.GE.F (ACACAGCTGACACCCAGGTAGGCA; SEQ ID NO:6). RT-PCR fragments containing the human T/G site were amplified by using the primer pairs H7.830 (CCTACCGCTACTCAGGCGTGAACC; SEQ ID NO: 3) and H7.1110 (TTCCCATTGAGCCTCCTTGATGAAG; SEQ ID NO:7) or the primer pair Oli4 (ATGAAGCGGCCGCCAAAGCGC SEQ ID NO: 8) and Oli3+3 (TCAGGCGTGAACCTGACAGGATTC; SEQ ID NO:9). RT-PCR products containing the mouse GluR7 C/T site were obtained by performing standard RT-PCR reactions using the primer pair M7.342 (GACCATCACCCATGTCCGAGAGAA; SEQ ID NO:10) and M7.662 (GGAGCCCATTCCMACCAGAAGCT; SEQ ID NO:11). The T/G polymorphism identified in the human GluR7 gene and mRNA was studied by using a cycled primer extension assay with the dideoxy terminator ddTTP and the primer H7.PE/T/G (GGCTGCAGGCAGCTCCC; SEQ ID NO:12). The C/T polymorphism identified in 129/SvEvTac×CBA/CaJ Fl generation mice was analyzed by performing primer extension assays using the dideoxy terminator ddATP. The primer M7.PE.C/Ta (CGTACATCCAGATGTCC; SEQ ID NO:13) was used for these assays.

cDNA synthesis and PCR: Total RNA and genomic DNA were prepared using the TRIzol® reagent (Life Technologies; Rockville, Md.). To avoid cross contamination, brain tissue samples were homogenized with disposable generator probes (Omni; Warrenton, Va.). cDNA was generated using the Thermoscript™ RT-PCR system according to manufacturer's instructions (Life Technologies; Rockville, Md.). The oligonucleotides used for priming the cDNA synthesis were complementary to the 3' untranslated region of the human, rat or mouse GluR7 transcript to ensure highest specificity. cDNA aliquots were used as template for standard PCR amplifications to obtain RT-PCR products covering the human and rat T/G, G/A sites, or the mouse C/T site. TAQ2000 DNA polymerase (Stratagene, San Diego, Calif.) was used for the amplification reactions. The RT-PCR primers were designed to amplify over at least one intron/exon border to avoid the amplification of genomic DNA sequences frequently present as contamination in total RNA preparations. To obtain genomic PCR fragments for the analysis of the T/G and G/A sites in the human GluR7 or rat GluR7 genes, PCR reactions were performed on genomic DNA. One of the PCR primers used was always complementary to intronic sequences to ensure gene specificity during amplification. GluR7 gene specific exonic primers were used to analyze the C/T polymorphism in the mice genome. When necessary, RT-PCR products or genomic PCR fragments were sub-cloned and inserts were sequenced.

Plasmids and site-directed mutagenesis: The human GluR7 cDNA clone was obtained from Sibia Neurosciences, San Diego, Calif. The thymine residue at the T/G site of this human GluR7 (S310) cDNA clone, encoding the serine variant, was replaced by PCR based site-directed mutagenesis with guanine, to obtain the human GluR7 (A310) cDNA, coding for the alanine isoform. The presence of introduced mutations and the correct sequence of the PCR amplified DNA sequence was verified by DNA sequencing.

Electrophysiology: Transfection of HEK 293 cells and whole cell patch-clamp analysis of human GluR7 (A310) or GluR7 (S310) or rat GluR7 (S310) receptor responses were carried out as described elsewhere (Schiffer, et al. (1997) Neuron, 19, 1141–1 146; herein incorporated by reference in its entirety).

Example 2

Detection and Analysis of Kainate Receptor Subunit GluR 7 Encoding DNA and RNA in Human Brain GluR7 polymorphisms at the T/G, G/A or C/T site in human, rat or mouse GluR7 cDNA (mRNA) and in corresponding genomic DNAs were analyzed with a cycled primer extension assay with dideoxy terminators, as described previously (Schiffer and Heinemann, (1999) Anal Biochem, 276: 257–260). $^{32}$P-end-labeled primers complementary to sequences upstream or downstream of the polymorphic nucleotide sites were hybridized to RT-PCR fragments or genomic PCR fragments and enzymatically extended in the presence of dideoxy terminators. Length of extended primers was determined by the type of nucleotide at the polymorphic nucleotide site. The extended primers were separated by electrophoresis in 15% denaturing polyacrylamide-8 M urea gels. Phosphorimaging analysis of the dried gels was used to quantify the relative amount of each allele in the analyzed DNA fragment fraction. Relative expression of GluR7 allelic mRNAs was assessed by calculating a ratio between the relative DNA fragment amounts detected for the two alleles. Further details may be found in Shiffer et al., J Neurosci (2000) 20:9025–9033.

The location of a single nucleotide polymorphism in the gene GRIK3 encoding the human glutamate receptor subunit GluR7 was analyzed using primer extension with dideoxy terminators As described, a $^{32}$P-labeled primer was annealed to GluR7 specific RT PCR (derived from cDNA) or genomic PCR products containing the T/G site, and extended in the presence of ddTTP. Primer extension at the T/G site in cDNA from fetal brains and in genomic DNA from an adult brain both showed two extended primer products, a 21 and 27 mer, indicating that the human GluR7 gene GRIK3 is polymorphic at the T/G site.

The T/G site is in the GRIK3 gene is at nucleotide position 928 in EAA5 cDNA, GenBank Accession number U16127. Nucleotide and amino acid sequences of the region surrounding the T/G site in the GluR7 cDNA/GRIK3 predicts alternating amino acids in the GluR7 receptor protein at amino acid position 310 (serine for T928 and alanine for G928) (amino acid position number 1 is the methionine for the signal peptide in the GluR7 receptor precursor).

Mouse whole brain cDNA library 49 was screened with a 0.7 kb cDNA probe corresponding to the 3' end of the rat GluR7 cDNA, to obtain sequence information of the mouse GluR7 cDNA. A 1.8 kb fragment was isolated representing the 3' half of the GluR7 cDNA. The sequence has been submitted to Genbank with the Accession Number AF245444. A transcribed nucleotide variation has been identified in the GluR7 gene between mouse strains CBA/CaJ and 129/SvEvTac using the Mutation Screener Kit from Ambion, Inc. (Austin, Tex.). The nucleotide variation is localized at nucleotide position 1686 corresponding to the homologous rat GluR7 cDNA (A in start codon of rat GluR7 cDNA is referred as nucleotide one). The CBA/CaJ mouse strains contain a cytosine (C) at this position in contrast to 129/SvEvTac strains, which contain a thymine (T).

Two nucleotide variations found in cDNAs coding for the human GluR7 receptor had previously been postulated to result from RNA editing (Nutt, et al. (1994) Receptors Channels, 2, 3 15–326). In the human GluR7 cDNA, guanine nucleotides were found at cDNA position 928 and adenine nucleotides were found at position 1055; these nucleotides did not match the reported human genomic sequences of thymine and guanine, respectively. In the rat GluR7 cDNA, a guanine nucleotide was previously identified at both corresponding sites (Bettler, et al (1992) *Neuron,* 8, 257–265; Lomeli, et al. (1992) *FEBS Lett,* 307, 139–143). Because RNA editing at the well-characterized Q/R site in GluR2, GluR5 and GluR6 subunits proceeds to a similar extent in rat and humans (Seeburg (1996) J Neurochem, 66, 1–5), it was first determined whether residues in the rat GluR7 cDNA also showed variability. Primer extension assays were performed with ddTTP as a dideoxy terminator on reverse transcription -polymerase chain reaction (RT-PCR) products as described in Schiffer and Heinemann, (1999) *Anal Biochem,* 276, 257–260 (herein incorporated by reference in its entirety) to determine whether similar nucleotide variations existed in rat GluR7 mRNAs. The cDNA products were obtained by amplifying a region that included the putative thymine/guanine (T/G) site at position 928 and the guanine/adenine (G/A) site at position 1055. The GluR7 cDNAs used as template for the amplifications were derived from embryonic (E18) and adult (Ad) whole rat brain total RNA.

Primer extension assays did not detect a nucleotide variation at either site in the rat GluR7 cDNA. The detection of only one 29-mer band (G at T/G site) and only one 23-mer band (G at G/A site) indicated that GluR7 mRNA sequences in the rat brain are not variable at these sites. These results demonstrate that the T/G and G/A sites in rat GluR7 transcripts are unlikely to be modified by RNA editing. Four genomic DNA fragments from rat that include the T/G or G/A sites were amplified and subcloned. In agreement with the primer extension assay results (and the sequence from the cloned cDNAs), only guanine residues were found in the GluR7 gene at these sites.

To further characterize the proposed editing events in the human GluR7 receptor, the T/G and G/A sites in human GluR7 mRNA were analyzed using the primer extension assay with ddTTP as dideoxy terminator. RT-PCR reactions were performed on human fetal whole brain total RNA that represented pooled RNAs derived from 13 brains. Primer extension analysis of the obtained RT-PCR products revealed a nucleotide variation at the T/G site. Thus, both a 21 base pair (T-containing) and 27 base pair (non-T-containing) extension product were observed. The same result was obtained in two independent assays and is consistent with the result of Nutt et al., (1994, supra). Phosphorimaging analysis determined that a thymine was present at the T/G site in 92% of the analyzed fetal RT-PCR products. In contrast, a nucleotide variation at the G/A site could not be detected in three independent primer extension assays using genomic DNA samples from 15 individuals.

To determine whether the nucleotide variation at the T/G site resulted from RNA editing or a genetic polymorphism, genomic DNA sequences from the human GluR7 gene (GRIK3) which contain the GluR7 T/G site were amplified, and additional primer extension assays were performed. The genomic DNA analyzed was derived from one single individual. The genomic primer extension assay demonstrated that thymine was incorporated in approximately 50% of the extension products, and that a nucleotide other than thymine was present in the rest of the extension products. This observation is consistent with the interpretation that the individual was heterozygotic at this site in the GRIK3 alleles. Sub-cloned RT-PCR (cDNA) and genomic PCR products were sequenced to verify the results of the primer extension assays. As expected, guanine and thymine residues were found at the T/G site in both the GluR7 cDNAs and the gene. Analysis of five genomic clones revealed three clones containing a guanine and two clones containing a thymine at the T/G site. Analysis of ten cDNA clones revealed one containing a guanine and nine containing a thymine at the T/G site. Additional primer extension assays with ddGTP as the dideoxy terminator were carried out on genomic PCR fragments derived from three identified individuals that were heterozygotic for the T/G polymorphism. In all three samples, guanine was identified in approximately 50% of the extension products. These results demonstrate that the T/G nucleotide variation is caused by a bi-allelic polymorphism in the human GluR7 gene and that the T/G site contains no nucleotide types other than guanine or thymine. This exonic nucleotide variation predicts either a serine (S) or alanine (A) at position 310 (S/A site) in the amino-terminal extracellular domain of the GluR7 receptor subunit.

Single nucleotide polymorphisms (SNPs) are useful tools in genetic studies that seek to identify candidate genes for human diseases (Gusella (1986) *Ann Rev Biochem,* 55, 83 1–854). An initial study was conducted to determine the allele frequency and genotype distribution of the GluR7 T/G polymorphism in the human population. The genomes of 35 healthy control Caucasians were analyzed and the nucleotide identity at the T/G site of each GluR7 allele was determined. The genotypes for each individual were obtained by performing primer extension assays with dideoxy terminators on genomic PCR fragments derived from these individuals. The results are summarized in Table 1.

TABLE 1

| Genotype | Number | Percentage (%) |
|---|---|---|
| T/T | 17 | 48.6 |
| T/G | 15 | 42.8 |
| G/G | 3 | 8.5 |
| Allele Frequency | | |
| T | | 0.7 |
| G | | 0.3 |

The frequency of the T and G allele among the analyzed group of 35 individuals (21 female and 14 male) was estimated as 0.70 and 0.30, respectively. 42.8% of the individuals were heterozygous for the T/G polymorphism in the GRIK3 gene, 48.6%were homozygous for the T allele and 8.6% were homozygous for the G allele. The observed genotype distributions correlated well with the Hardy-Weinberg equilibrium, as predicted from the observed allele frequencies. These results suggest that the T/G polymorphism in the GluR7 gene is common in the analyzed portion of the human population (heterozygosity is estimated to be 0.428). Although evidence for a genetic polymorphism at the G/A site was not found, the existence of a rare genetic polymorphism at this site of the GRIK3 gene can not be entirely excluded. The identified polymorphism at the T/G site of the GluR7 gene is the first example of a genetic polymorphism that affects the primary structure of a human ionotropic glutamate receptor subunit.

The level of expression of human GluR7 receptor subunits isoforms was analyzed in human brain. Human genetics studies have recognized the relevance of genomic imprinting for neurobehavioral and developmental disorders of the CNS (Falls et al., (1999) *Am J. Pathol,* 154:635–647. Genomic imprinting is an epigenetic mechanism that silences expression of an allele dependent if this allele is inherited from the father (paternal) or the mother (maternal). To test if the human GluR7 gene (GRIK3) is affected by genomic imprinting, the expression of GluR7 alleles in human brain was studied. The T/G polymorphism identified in the human GluR7 gene served in these experiments as a genetic marker to distinguish between differential expression of GluR7 alleles.

First, the GluR7 allele expression levels in total RNA isolated from brain tissue samples derived from nine individuals heterozygous for the T/G polymorphism (three fetuses and six adults) were analyzed. The brain region from which the samples were derived was not identified for these individuals. The total RNA isolated from each individual brain sample was reverse transcribed with GluR7 specific primers, and the cDNA was used as template to obtain pools of RT-PCR products covering the T/G site of the GluR7 mRNA. Each pool of RT-PCR products contained DNA fragments that had either a T or G at the T/G site, because only individuals heterozygous for the T/G polymorphism were analyzed. Individual RT-PCR product pools were used as template for the cycled primer extension assay with the dideoxy terminator ddTTP to determine the ratio between the T allele and G allele derived PCR fragments in these pools. It was assumed that the relative proportion of the T or G allele in the analyzed DNA fragment pools reflected the relative expression level in the brain tissue samples. In this study, the term "unequally expressed" was used when the relative GluR7 allele expression levels, differed by more than 1.20 fold from the ideal expected equal expression.

Results reveal that GluR7 alleles are unequally represented in most of the RT-PCR product fractions. In six samples, the estimated T/G allele ratio varied between 0.30 and 0.73, indicating a lower expression of the T allele compared to the G allele. In contrast, one sample showed a T/G ratio of 4.7, indicating a higher expression of the T allele compared to the G allele. Two of the 9 analyzed samples had a ratio of 0.89 and 0.87, reflecting a nearly equal GluR7 allele expression. In summary, seven of the nine analyzed samples showed a 1.4 to 4.7 fold reduction in the expression levels of one GluR7 allele compared to the second allele. All assays shown were repeated at least three times and gave reproducible results. The estimated standard deviation for each analyzed sample ranged between 0.9 % and 5.2 % (n=3). Furthermore, additional control assays on RT-PCR products synthesized in independent cDNA synthesis and PCR reactions gave similar results. Unequal expression as the result of polyploidy was excluded, because genomic PCR fragments derived from each sample, had the expected T/G ratio of approximately 1.

To further analyze the unequal expression of GluR7 mRNA, human brain total RNA samples isolated from temporal lobes of neuropsychiatric patients matched for age and post mortem interval were analyzed. Twelve individuals, heterozygous for the T/G polymorphism in the GluR7 gene, were identified by analyzing genomic DNA with the cycled primer extension assay. The corresponding 12 total RNA samples were analyzed as described herein and the relative GluR7 allele expression levels determined. Similar to the previous observation, unequal expression levels in most of the analyzed samples was detected. Six samples showed a T/G ratio between 0.52 and 0.72, in contrast to four samples that showed T/G ratios of 1.27, 1.43, 3.0, and 5.8. Two samples showed a more equal expression of GluR7 alleles with a T/G ratio of 1.01 and 0.78. These results indicate that the T and G allele of the GluR7 gene were unequally expressed in most of the analyzed human temporal lobes. The detection of unequal GluR7 allele expression in brain samples matched for brain region and age, suggests that unequal GluR7 allele expression occurs frequently in human brains. Furthermore, it appears possible that the GluR7 gene is affected by genomic imprinting.

The observation that unequal GluR7 allele expression occurs only in a subset of samples and that the difference between the GluR7 T allele and G allele expression levels varied over a wide range could be the result of brain region specific genomic imprinting of the GluR7 gene. Therefore, various brain regions isolated from individual human brains were analyzed to determine the relative expression level of GluR7 alleles. Genotyping of brain samples from adult individuals without disease history identified two brains which were heterozygous for the T/G polymorphism in the GR1K3 gene. Total RNA from frontal cortex, occipital cortex, parietal cortex, mesencephalon, cerebellum, basal ganglion and thalamus was isolated and analyzed for relative GluR7 allele expression levels using RT-PCR in combination with the cycled primer extension assay with dideoxy terminator ddTTP (as described herein). In one brain (Brain A), a large difference in the expression levels of GluR7 alleles and varying between brain regions was observed. The relative T and G allele expression levels varied between a factor 1.8 and 12.7 fold. In particular, the cerebellum expressed 12.7 fold less G allele than T allele. All other brain regions showed strong reduction of the G allele expression levels, with the exception of the frontal cortex, where a two fold higher expression level of the G allele compared to the T allele was detected. As a control, the T/G site in genomic DNA from brain A was analyzed revealing equal T and G allele representation in the genomic PCR product fraction. These results also exclude the possibility that the T/G polymorphism had a differential effect on the amplification efficiency of PCR products containing a T or G at the T/G site. These results indicate that GluR7 allele expression levels can differ in a human brain by up to 12.7 fold, and that these differences can be variable between brain regions.

In contrast, analysis of the same brain regions from a second brain (brain B) did not show significant differences in GluR7 expression levels. Most of the analyzed brain regions of brain B showed nearly equal expression levels of GluR7 alleles. Only three regions showed a T/G ratio between 0.5 and 0.63.

The relative GluR7 allele expression levels were examined in cerebelli heterozygous for the T/G polymorphism since this brain area showed the largest variability in T/G expression in Brain A. Large differences in GluR7 allele expression levels were not detected in the additional seven cerebelli examined. Two cerebelli showed a T/G ratio of 0.52 and 0.62. The other analyzed cerebelli expressed the T and G allele at T/G ratios of 0.85 to 1.2.

In 27 brain samples that showed unequal allele expression, the detected unequal expression of one GluR7 allele was not strictly correlated with a particular nucleotide type (T or G) found at the T/G site, although the T allele had a lower expression level than the corresponding G allele. Eighteen brain samples derived from 16 brains showed a lower expression of the T allele, in contrast to nine brain samples derived from six brains that showed a lower expression of the G allele. Fourteen brain samples showed allele expression which was not considered unequal. These results are summarized in Table 2.

TABLE 2

| GluR7 allele expression level differences | T/G ratios <1 | T/G ratios >1 | Total |
|---|---|---|---|
| 0.8–1.2 fold | — | — | 14 |
| 1.2–2.0 fold | 16 | 2 | 18 |
| 2.0–12.7 | 2 | 7 | 9 |

Genomic imprinting, a mechanism that causes silencing of one allele depending on the parental origin, is a mechanism which gives rise to the unequal expression of GluR7 alleles in human brains. Genomic imprinting of genes is specifically regulated by developmental stage and cell type. Furthermore, it has been observed in humans that some genes are not imprinted in every studied individual (Bunzel, et al. (1998) *Brain Res Mel Brain Res,* 59, 90–92; Nishiwaki, et al. (1997) *Jpn J Hum Genet,* 42, 205–211; Xu, et al (1993) *Biochem Biophys Res Commun,* 197, 747–754). It has been suggested that variability in the efficiency of imprinting results from the heterogeneity of the human genome. In contrast, the homologue mouse genes are imprinted in every individual mouse analyzed, indicating that the genetic background affects genomic imprinting.

Because the genomic imprinting mechanism is highly conserved between human and mice, allele expression in a mouse model with isogenic background was examined. To test if the murine GluR7 gene is affected by genomic imprinting, genetically divergent mice strains were examined to identify a transcribed nucleotide variation in GluR7 genes between strains. GluR7 allele expression was evaluated in F1 generation 129SvEvTac×CBA/CaJ mouse brains. The mouse GluR7 cDNA sequence was only partially available, requiring an initial screen of a mouse brain cDNA library to clone the 3' half of the mouse GluR7 receptor cDNA. The 1.8 kb GluR7 cDNA sequence obtained, allowed a screen of mice strains for nucleotide variations in the GluR7 mRNA using the mutation screener kit from Ambion Inc. (Austin, Tex.)(Goldrick et al., (1996) *Biotechniques* 21:106–112).

A silent nucleotide variation in the GluR7 open reading frame was identified between mice strains 129/SvEvTac and CBA/CaJ at mRNA nucleotide position 1686 (the adenosine (A) in the start codon ATG is referred as nucleotide +1, numbering corresponding to the rat GluR7 cDNA sequence). CBA/CaJ mice strains contain a cytosine (C) at this position in contrast to 129/SvEvTac strains, which contain a thymine (T). Male 129/SvEvTac mice were crossed with female CBA/CaJ mice, and female 129/SvEvTac mice were crossed with male CBA/CaJ mice, to obtain F1 generation mice that were heterozygous for the C/T polymorphism. The relative GluR7 allele expression levels were analyzed in F1 generation mice at postnatal ages P3, P13 and P21. Total RNA was isolated from P3 whole brains, P13 cerebelli, and P21 cortex, cerebelli, and hippocampi. GluR7 specific primers were used to synthesize cDNA and to amplify RT-PCR products covering the C/T site. The cycled primer extension assay with dideoxy nucleotide ddATP was used to quantify the relative expression level of GluR7 alleles and to analyze the mouse GluR7 gene (Schiffer and Heinemann (1999) *Anal Biochem,* 276, 257–260.).

No differences in GluR7 allele expression levels were detected in the mouse brain samples analyzed. The C and T allele of GluR7 were equally expressed in six tissue samples from two P21 mice brains, with estimated C/T ratios varying between 0.97 and 1.07. Also, no difference in GluR7 allele expression level was detected in brain tissues from crosses in which the sex and genotype relationships were exchanged. F1 generation mice from crossing male CBA/CaJ mice with female 129/SvEvTac mice were denoted as MC, in contrast to FC mice, which resulted from crossing female CBA/CaJ mice with male 129/SvEvTac mice. In addition, similar results were obtained analyzing the brain tissue samples from mice at age P3 and P13. The detected C allele/T allele ratios only varied between factor 0.9 and 1.1. These results show that the GluR7 alleles in F1 generation mice, derived from crosses of 129/SvEvTac mice with CBA/CaJ mice, are not unequally expressed. In particular, these results demonstrate that in an isogenic genetic background GluR7 allele ratios can be detected, with a primer extension assay, without variations bigger than 0.1. Although it appears unlikely, it is possible that the GluR7 receptor gene is genomic imprinted in mice that have a genetic background which is different from that of 129/CBA mice.

An exonic genetic T/G polymorphism in the human GRIK3 gene which codes for the glutamate receptor subunit GluR7 accounts for the expression of GluR7 receptor variants. Analysis of the genomes of 35 healthy Caucasians revealed an estimate for the frequency of the T and G allele and the distribution of the genotypes in this portion of the human population. The analyzed group showed a higher frequency of the T allele (0.70) than the G allele (0.30), in contrast to rats, which contain only the G allele. These results show that in Caucasians about 70% of the GRIK3 alleles express receptors with a serine at the S/A site at position 310, while the rat GluR7 receptors always contain an alanine at this site.

Example 3

Detection and Analysis of GluR7 Kainate Receptor Subunit Encoding DNA and RNA in Human Brain This example provides methods for evaluating the activity of the GluR7 receptor. The rat GluR7 receptor subunit forms functional homomeric receptor channels with low sensitivity to glutamate (Schiffer, et al (1997) *Neuron,* 19:1141–1146). Because the T/G polymorphism occurs within the coding sequence of GluR7, differences in the functional behavior of the GluR7 glutamate receptors were examined. Functional properties of human GluR7 receptors were compared with those of rat GluR7 receptors. The detected nucleotide variation at the T/G site lies in a codon that encodes serine when thymine is present, or alanine when guanine is present. The affected amino acid at position 310 is localized in the amino-terminal extracellular domain of the GluR7 receptor protein (Nutt et al., 1994, supra). This domain of glutamate receptors has been shown to affect receptor desensitization (Krupp et al., (1998) *Neuron,* 20:317–320; Nutt et al., 1994, supra) and participate in ligand binding (Stern-Bach, et al. (1994) *Neuron,* 13: 1345–1357; Armstrong, et al. (1998) *Nature,* 395: 913–917). The thymine residue at the T/G site of the human GluR7 (S310) cDNA, encoding the serine variant, was replaced by PCR based site-directed mutagenesis with guanine, to obtain the human GluR7 (A310) cDNA, coding for the alanine isoform. Human embryonic kidney HEK 293 cells were transiently transfected with the GluR7 (A310) or GluR7 (S310) cDNAs and receptor currents evoked by fast-application of glutamate (30 mM) were recorded in whole-cell patch-clamp configuration.

Homomeric human GluR7 (A310) or GluR7 (S310) receptors had similar functional properties. The mean peak amplitudes of glutamate evoked currents estimated for the human GluR7 (A310) and GluR7 (S310) receptors were 1.9±0.3 nA with a 10%–90% rise time of 1.4±0.2 ms, and 1.31±0.2 nA with a 10%–90% rise time of 1.3±0.1 ms, respectively. These data were not different from each other or from that of the previously characterized rat GluR7a (S310) receptor (1.1±0.2 nA mean peak amplitude and 1.4±0.1 ms rise time)(Schiffer et al., 1997, supra). Glutamate evoked currents from the human GluR7 (A310), GluR7 (S310) and rat GluR7a (S310) receptor desensitized with similar time courses ($\tau_{des}$ of 7.1±0.7 ms, 6.3±0.4 ms, and 8.4±0.5 ms, respectively). Dose response analyses of peak currents evoked by L-glutamate gave $EC_{50}$ values for human GluR7 (A310) and GluR7 (S310) receptors of 4.1 mM and 3.8 mM, respectively. Interestingly, the estimated $EC_{50}$s for these GluR7 receptor isoforms were lower than that of rat GluR7a (S310) receptors ($EC_{50}$=7.5 mM in parallel experiments) although the amino acid sequence of the mature rat and human GluR7 (S310) receptor proteins differ by only 8 amino acids.

These results indicate that the replacement of alanine for serine at amino acid position 310 in the human GluR7 receptor does not affect receptor responses to glutamate in vitro. However, the human alanine and serine variant of the GluR7 receptor may have distinct functional behavior when expressed in the brain. The predicted amino acid variation in the GluR7 receptor is localized in the first half of the extracellular domain. The function of this domain is not well understood, but it may play a role in receptor assembly or determining channel kinetics. The predicted amino acid alteration at the S/A site of the human GluR7 receptor is conservative, but a similar amino acid difference in the extracellular region between membrane domains 3 and 4 of GluR5 and GluR6 receptors alters channel desensitization kinetics (Swanson, et al. (1997) *Neuron*, 19, 9 13–926).

Example 4

Association of the Kainate Receptor Subunit GluR7 Gene with Depressive Disorders Subjects: The genomic DNA samples analyzed are part of the National Institute of Mental Health (NIMH) Bipolar Disorder Genetics Initiative, representing 153 families with at least one affected sib-pair, contained in release 1.1 of the bipolar disorder data set. The phenotypic status of analyzed individuals was ascertained according to the third edition of the diagnostic statistical manual (DSM-III-R) for bipolar I disorder and schizoaffective disorder (bipolar type), and according to research diagnostic criteria (RDC) for bipolar II disorder and recurrent unipolar depressive disorder.

Determination of GluR7 genotype: The T/G polymorphism in the human GluR7 gene GRIK3 was analyzed as follows: The T/G polymorphism is detectable in the human population as a restriction-fragment length polymorphism (RFLP) using the restriction enzyme SmaI. The GluR7 G-allele (CCCGGG) is cleaved by SmaI, in contrast to the T-allele (CCCGGT). The primer pair H7.954 (5'- TCACCCAGCCGCCTTACCATCATC; SEQ ID NO:14) and Oli3+3 (5'-TCAGGCGTGAACCTGACAGGATTC; SEQ ID NO:9) was used to amplify a 155 base pair genomic DNA fragment from the GluR7 gene. The sequence of primer H7.954 is complementary to the 3' intron/exon border of the T/G site-containing exon thereby ensuring gene-specific amplification. PCR reactions were catalyzed by Taq DNA polymerase (Qiagen, Valencia, Calif.) in 25 $\mu$l volume reactions. The standard reactions included 250–500 ng genomic DNA, 45 pmol of each primer, 5% glycerol, 0.8U Taq DNA polymerase, and were not overlaid with mineral oil. The following PCR profile was applied: step 1: denaturing for 5 min at 94° C.; step 2: annealing for 2 min at 57° C.; step 3: elongation for 2 min at 72° C.; step 4: denaturing for 1 min at 94° C.; step 5: annealing for 25 sec at 57° C.; step 6: elongation for 10 sec at 72° C. with 30 cycles (steps 4–6) in a thermocycler PTC100 with heated lid (MJ Research, Inc., Watertown, Mass.). The restriction enzyme SmaI (5U) was directly added to the completed PCR reactions. The reactions were incubated at room temperature for at least two days to obtain complete SmaI digestion of the PCR products. The digested PCR products were separated on 1.5% agarose gels in the presence of ethidium bromide and analyzed under UV light. Analyzed samples containing two GluR7 T-alleles (T/T genotype) showed only uncleaved, 155 base pair PCR products; samples containing GluR7 T- and G-alleles (T/G genotype) showed a 155 base pair PCR product and a 103 base pair cleavage product; samples containing two GluR7 G-alleles (G/G genotype) showed only a 103 base pair cleavage product. Cleavage products of 52 base pairs were not detectable because they migrated in gels with the primers. All samples initially assigned a T/T genotype were reanalyzed to verify the result.

Transmission-disequilibrium test (TDT) and statistical analysis: The transmission-disequilibrium test (TDT) was applied as described by Spielman et al. ((1993) Am. J. Human Genetics, 52:506–516; herein incorporated by reference in its entirety). Six parental T/G genotypes were inferred from the genotypes of their offspring and included in the analysis. The statistical significance of the TDT results and the case-control analysis results were tested by using the McNamar's chi-square test and the standard chi-square test, respectively.

The T/G polymorphism in the GluR7 gene was used as a genetic marker to test if the GluR7 gene is associated with neurological disorders. First, the distribution of the GluR7 T/G polymorphism in individuals from various disease groups and related controls was analyzed to detect disease related differences in allele frequency and genotype distribution. Small differences in the genotype distribution of the T/G polymorphism were observed between the control group and each of the major depression and bipolar disorder groups. Based on this initial observation, a family-based association study was performed to test if the GluR7 gene or a closely linked chromosomal locus could be involved in mood disorders. The transmission disequilibrium test (TDT), which detects linkage of a genetic marker and a disease locus in the presence of linkage disequilibrium of the two loci was used. (Spielman et al., (1993) *Am. J. Human Genetics*, 52:506–516 and Spielman and Ewens, (1996) *Am. J. Human Genetics*, 59:983–989).

A total of 928 genomic DNA samples obtained from the National Institute of Mental Health (NIMH) Bipolar Disorder Genetics Initiative, representing 153 multiplex families with at least one affected sib-pair, were genotyped for the T/G polymorphism in the human GluR7 gene as described herein. Polymerase chain reaction and restriction analysis was used for genotyping the samples because the T/G polymorphism in the GluR7 gene is detectable as restriction-fragment length-polymorphism (RFLP). The collected data for the TDT were separated and independently analyzed according to three diagnostic categories: recurrent unipolar depressive disorder, bipolar I disorder and bipolar II disorder. TDT analysis suggests that the GluR7 gene or a closely linked chromosomal locus might be involved in major depression. 34 of 50 offspring/parent triads analyzed showed preferential transmission of a GluR7 T-allele from each heterozygous (T/G) parent to offspring affected with recurrent unipolar depressive disorder (TDT=6.48; df=1, P=0.011). This TDT analysis also found statistically significant evidence that GluR7 or a closely linked chromosomal locus might be involved in bipolar II disorder. In this disease category, however, preferential transmission of a GluR7 G-allele from each heterozygous (T/G) parent to affected offspring was observed (TDT=5.00; df=1, P=0.025). In contrast, the TDT analysis of 165 offspring/parent triads did not show a preferential transmission of a GluR7 allele from heterozygous (T/G) parents to offspring affected with bipolar I disorder (TDT=0.15; df=1, P=0.752). Therefore, the chromosomal locus containing the GluR7 gene is probably not involved in bipolar I disorder. Additionally, this result also excludes the possibility that the observed transmission disequilibrium in the tested disease categories is caused by meiotic drive. The control TDT analysis, testing for GluR7 alleles transmitted from heterozygous (T/G) parents to healthy offspring was not informative because of the low number of suitable offspring/parent triads.

GluR7 allele frequencies and genotype distributions were assessed in individuals in each diagnostic category (recurrent unipolar depressive disorder, bipolar I disorder, bipolar II disorder) and control individuals (never mentally ill). Similar to the results of the TDT test, a significant association between recurrent unipolar depressive disorder and the GluR7 gene was detected Table 3, which summarizes the association of T/G genotype with disease in the tested families shows significant association of the T/T genotype with recurrent unipolar depressive disorder (P=0.151) and a weaker association of the G/G genotype with bipolar II depressive disorder (P=0.659).

TABLE 3

GluR7 Genotype Frequency in 153 Families

Genotype Distribution Frequency n (%)

|  | N | T/T | T/G | G/G | P |
|---|---|---|---|---|---|
| Recurrent unipolar depressive disorder | 139 | 84 (60.4) | 48 (34.5) | 7 (5.0) | 0.151 |
| Bipolar I disorder | 374 | 178 (47.6) | 174 (46.5) | 22 (5.9) | 0.659 |
| Bipolar II disorder | 112 | 44 (39.3) | 57 (50.9) | 11 (9.8) | 0.332 |
| Control | 127 | 62 (48.8) | 55 (43.3) | 10 (7.8) |  |

The 928 T allele frequency for GluR7 was significantly increased in individuals in the disease category recurrent unipolar depressive disorder ($\chi^2$=3.62, df=1, P=0.057) compared to the control category. No differences in allele frequencies were detected between the disease category bipolar I disorder and the control category ($\chi^2$=0.13, df=1, P=0.908). The statistics for the bipolar II disorder category showed a P value indicating that the G allele frequency is increased in this disease category ($\chi^2$=1.79, df=1, P=0.180). These results are consistent with TDT test results showing a statistically significant preferential transmission of the G allele to bipolar II disorder affected offspring. The results of T and G allele frequency are summarized in Table 4.

TABLE 4

GluR7 Allele Frequency in 153 Families

| | Allele Frequency N (%) | | |
|---|---|---|---|
| | T | G | P |
| Recurrent unipolar depressive disorder | 216 (77.7) | 62 (22.3) | 0.057 |
| Bipolar I disorder | 530 (70.9) | 218 (29.1) | 0.971 |
| Bipolar II disorder | 145 (64.7) | 79 (35.3) | 0.180 |
| Control | 179 (70.5) | 75 (29.5) | |

Thus, the results of the above-described family based association study establish an association between GluR7 receptors or a closely linked chromosomal locus and recurrent unipolar depressive disorder as well as bipolar II disorder, but not in bipolar I disorder.

The invention thus has been disclosed broadly and illustrated in reference to representative embodiments described above. Those skilled in the art will recognize that various modifications can be made to the present invention without departing from the spirit and scope thereof. All publications, patent applications, and issued patents, are herein incorporated by reference to the same extent as if each individual publication, patent application or issued patent were specifically and individually indicated to be incorporated by reference in its entirety.

What is claimed is:

1. A method of determining predisposition of a subject to a recurrent unipolar depressive disorder, said method comprising determining in a biological sample of a subject, a human kainate receptor subunit GluR7 allelic genotype, said genotype being homozygosity for a thymine containing nucleotide at position 928 (928T/T), wherein the parents of said subject are T/G heterozygous at position 928 (928T/G) and wherein the presence of the homozygosity for thymine at the 928 position indicates that the subject is predisposed to recurrent unipolar depressive disorder.

2. A method of determining predisposition of a subject to a recurrent unipolar depressive disorder, said method comprising determining in a biological sample from a subject, a human kainate receptor subunit GluR7 allelic phenotype, said phenotype being homozygosity for a seine at amino acid position 310 (310 Ser/Ser), wherein the parents of said subject are heterozygous at position 310, said heterozygosity being 310 Ser/Ala and wherein the presence of the homozygosity for a seine at amino acid position 310 indicates that the subject is predisposed to recurrent unipolar depressive disorder.

3. A method of determining predisposition of a subject to a bipolar II depressive disorder, said method comprising determining in a biological sample of a subject, a human kainate receptor submit GluR7 allelic genotype, said genotype being homozygosity for a guanine containing nucleotide at position 928 (928G/G), wherein the parents of said subject are T/G heterozygous at position 928 (928T/G) and wherein the presence of the homozygosity for a guanine at the 928 position indicates that the subject is predisposed to bipolar II depressive disorder.

4. A method of determining predisposition of a subject to bipolar II depressive disorder, said method comprising determining in a biological sample of a subject, a human kainate receptor subunit GluR7 allelic phenotype, said phenotype being homozygosity for alanine at amino acid position 310 (310 Ala/Ala), wherein the parents of said subject are heterozygous at position 310 said heterozygosity being 310 Ser/Ala and wherein the presence of the homozygosity for an alanine at amino acid position 310 indicates that the subject is predisposed to bipolar II depressive disorder.

5. The method of claim 1 wherein said subject has at least one sibling affected with said disorder.

6. The method of claim 2 wherein said subject has at least one sibling affected with said disorder.

7. The method of claim 3 wherein said subject has at least one sibling affected with said disorder.

8. The method of claim 4 wherein said subject has at least one sibling affected with said disorder.

9. The method of claim 1 wherein said sample is from blood.

10. The method of claim 3 wherein said sample is from blood.

* * * * *

UNITED STATES PATENT AND TRADEMARK OFFICE
CERTIFICATE OF CORRECTION

PATENT NO. : 6,664,055 B2
DATED : December 16, 2003
INVENTOR(S) : Schiffer et al.

It is certified that error appears in the above-identified patent and that said Letters Patent is hereby corrected as shown below:

Column 37,
Lines 16 and 20, delete "seine" and insert -- serine --.
Line 26, delete "submit" and insert -- subunit --.

Signed and Sealed this

Ninth Day of November, 2004

JON W. DUDAS
*Director of the United States Patent and Trademark Office*